(12) United States Patent
Kucharczyk et al.

(10) Patent No.: US 7,048,716 B1
(45) Date of Patent: May 23, 2006

(54) MR-COMPATIBLE DEVICES

(75) Inventors: John Kucharczyk, Minneapolis, MN (US); Charles L. Truwit, Wayzata, MN (US); Haiying Liu, Minneapolis, MN (US); Michael E. Moseley, Redwood City, CA (US)

(73) Assignee: Stanford University, Stanford, CA (US)

( * ) Notice: Subject to any disclaimer, the term of this patent is extended or adjusted under 35 U.S.C. 154(b) by 0 days.

(21) Appl. No.: 09/448,720

(22) Filed: Nov. 24, 1999

Related U.S. Application Data

(63) Continuation-in-part of application No. 09/131,031, filed on Aug. 7, 1998, now Pat. No. 6,272,370, and a continuation-in-part of application No. 08/857,043, filed on May 15, 1997, now Pat. No. 6,026,316.

(51) Int. Cl.
 A61M 5/178 (2006.01)
 A61M 29/00 (2006.01)
 A61B 5/05 (2006.01)

(52) U.S. Cl. .............................. 604/164.01; 604/96.01; 600/411; 600/423; 600/424

(58) Field of Classification Search ................ 604/20, 604/21, 93.01, 151–155, 96.01, 264, 164.01–164.09; 600/410–412, 420, 422–424, 431–433
See application file for complete search history.

(56) References Cited

U.S. PATENT DOCUMENTS

| | | | |
|---|---|---|---|
| 3,554,186 A | 1/1971 | Leksell et al. | |
| 3,705,938 A | 12/1972 | Hyman et al. | |
| 3,878,830 A * | 4/1975 | Bicher | 600/360 |
| 4,146,019 A * | 3/1979 | Bass et al. | 600/108 |
| 4,316,106 A | 2/1982 | Young et al. | |
| 4,338,571 A | 7/1982 | Young | |
| 4,351,341 A * | 9/1982 | Goldberg et al. | 606/194 |
| 4,448,195 A | 5/1984 | LeVeen et al. | |
| 4,572,198 A | 2/1986 | Codrington | |
| 4,710,403 A | 12/1987 | Krause et al. | |
| 4,767,973 A | 8/1988 | Jacobsen et al. | |
| 4,775,556 A | 10/1988 | Krause et al. | |
| 4,807,620 A | 2/1989 | Strul et al. | |
| 4,824,436 A | 4/1989 | Wolinsky | |
| 4,827,931 A | 5/1989 | Longmore | |
| 4,869,247 A | 9/1989 | Howard, III et al. | |
| 4,892,538 A | 1/1990 | Aebischer et al. | |

(Continued)

FOREIGN PATENT DOCUMENTS

EP 0442329 8/1991

(Continued)

OTHER PUBLICATIONS

Basser, P.J., "Interstitial Pressure, Volume, and Flow during Infusion into Brain Tissue", *Microvascular Research 44* (2), pp. 143-165, (Sep. 1992).

(Continued)

*Primary Examiner*—Kevin C. Sirmons
*Assistant Examiner*—Mark K Han
(74) *Attorney, Agent, or Firm*—Mark A. Litman & Associates, P.A.

(57) ABSTRACT

A catheter is used for medical treatments within an organism. The catheter comprises at least one lumen. Within the at least one lumen are at least two microcatheters, with at least one of the at least two microcatheters being connected to a source of liquid material to be delivered to the organism and another of the at least two microcatheters being connected to a system capable of effecting a medical treatment other than delivery of the liquid.

32 Claims, 6 Drawing Sheets

U.S. PATENT DOCUMENTS

| | | | |
|---|---|---|---|
| 4,914,608 A | | 4/1990 | LeBihan et al. |
| 4,917,097 A | * | 4/1990 | Proudian et al. ............ 600/463 |
| 4,922,924 A | | 5/1990 | Gambale et al. |
| 4,941,874 A | | 7/1990 | Sandow et al. |
| 4,967,765 A | * | 11/1990 | Turner et al. ............... 607/154 |
| 4,973,304 A | | 11/1990 | Graham et al. |
| 4,989,608 A | | 2/1991 | Ratner |
| 5,017,566 A | | 5/1991 | Bodor |
| 5,033,998 A | | 7/1991 | Corday et al. |
| 5,035,231 A | | 7/1991 | Kubokawa et al. |
| 5,050,607 A | | 9/1991 | Bradley et al. |
| 5,053,033 A | * | 10/1991 | Clarke .......................... 606/3 |
| 5,057,106 A | | 10/1991 | Kasevich et al. |
| 5,087,236 A | | 2/1992 | Morimoto |
| 5,087,256 A | | 2/1992 | Taylor et al. |
| 5,102,402 A | | 4/1992 | Dror et al. |
| 5,106,455 A | | 4/1992 | Jacobsen et al. |
| 5,106,627 A | | 4/1992 | Aebischer et al. |
| 5,120,322 A | | 6/1992 | Davis et al. |
| 5,125,888 A | | 6/1992 | Howard et al. |
| 5,154,179 A | | 10/1992 | Ratner |
| 5,167,625 A | | 12/1992 | Jacobsen et al. |
| 5,171,217 A | | 12/1992 | March et al. |
| 5,180,982 A | | 1/1993 | Zeiger |
| 5,203,337 A | * | 4/1993 | Feldman ..................... 600/463 |
| 5,211,165 A | | 5/1993 | Dumoulin et al. |
| 5,211,166 A | | 5/1993 | Sepponen |
| 5,226,902 A | | 7/1993 | Bae et al. ................. 604/892.1 |
| 5,263,963 A | | 11/1993 | Garrison et al. ............ 606/198 |
| 5,269,882 A | | 12/1993 | Jacobsen ................. 156/659.1 |
| 5,270,485 A | | 12/1993 | Jacobsen ................... 174/15.1 |
| 5,271,400 A | | 12/1993 | Dumoulin et al. ....... 128/653.2 |
| 5,273,622 A | | 12/1993 | Jacobsen ................. 156/659.1 |
| 5,303,707 A | | 4/1994 | Young ..................... 128/653.2 |
| 5,332,625 A | | 7/1994 | Dunn et al. ................. 428/409 |
| 5,354,279 A | * | 10/1994 | Hofling ................. 604/164.12 |
| 5,375,596 A | | 12/1994 | Twiss et al. ............. 128/653.1 |
| 5,387,410 A | | 2/1995 | Bosworth et al. .............. 424/9 |
| 5,389,195 A | | 2/1995 | Ouderkirk et al. .......... 156/643 |
| 5,415,163 A | | 5/1995 | Harms et al. ............ 128/653.2 |
| 5,425,382 A | | 6/1995 | Golden et al. ............... 128/899 |
| 5,427,103 A | | 6/1995 | Fujio et al. .............. 128/653.5 |
| 5,427,118 A | * | 6/1995 | Nita et al. .................. 600/585 |
| 5,429,132 A | | 7/1995 | Guy et al. ................ 128/653.1 |
| 5,441,481 A | | 8/1995 | Mishra et al. ................. 604/29 |
| 5,445,151 A | | 8/1995 | Darrow et al. ........... 128/653.3 |
| 5,451,744 A | | 9/1995 | Koopman et al. .......... 219/400 |
| 5,451,774 A | | 9/1995 | Jacobsen ............... 250/227.24 |
| 5,459,769 A | | 10/1995 | Brown ......................... 378/4 |
| 5,470,307 A | | 11/1995 | Lindall ........................ 604/20 |
| 5,487,739 A | | 1/1996 | Aebischer et al. ....... 604/890.1 |
| 5,492,534 A | | 2/1996 | Athayde et al. ............. 604/141 |
| 5,514,092 A | | 5/1996 | Forman et al. .............. 604/101 |
| 5,517,993 A | | 5/1996 | Unger et al. ............. 128/653.4 |
| 5,560,360 A | | 10/1996 | Filler et al. ............... 128/653.2 |
| 5,562,722 A | * | 10/1996 | Racz et al. .................. 607/117 |
| 5,569,197 A | | 10/1996 | Helmus et al. ............... 604/96 |
| 5,571,089 A | | 11/1996 | Crocker ....................... 604/102 |
| 5,572,132 A | * | 11/1996 | Pulyer et al. ............... 324/318 |
| 5,573,668 A | | 11/1996 | Grosh et al. ................. 210/490 |
| 5,580,575 A | | 12/1996 | Unger et al. ................ 424/450 |
| 5,590,654 A | | 1/1997 | Prince ..................... 128/653.4 |
| 5,607,418 A | | 3/1997 | Arzbaecher ............. 604/891.1 |
| 5,628,730 A | | 5/1997 | Shapland et al. ............. 604/21 |
| 5,646,185 A | | 7/1997 | Giaccia et al. ............... 514/548 |
| 5,647,361 A | | 7/1997 | Damadian ................ 128/683.2 |
| 5,654,864 A | | 8/1997 | Ritter et al. ................. 361/141 |
| 5,699,801 A | | 12/1997 | Atalar et al. ............. 128/653.2 |
| 5,702,372 A | | 12/1997 | Nelson ....................... 604/264 |
| 5,706,806 A | | 1/1998 | Kissinger ................... 128/632 |
| 5,707,335 A | | 1/1998 | Howard et al. |
| 5,713,358 A | | 2/1998 | Mistretta et al. |
| 5,713,359 A | | 2/1998 | Dumoulin et al. |
| 5,720,720 A | | 2/1998 | Laske et al. |
| 5,727,553 A | | 3/1998 | Saad |
| 5,728,079 A | | 3/1998 | Weber et al. |
| 5,741,248 A | | 4/1998 | Stern et al. |
| 5,744,958 A | | 4/1998 | Werne |
| 5,746,208 A | | 5/1998 | Prince |
| 5,779,694 A | | 7/1998 | Howard et al. |
| 5,782,764 A | | 7/1998 | Werne |
| 5,788,713 A | | 8/1998 | Dubach |
| 5,792,110 A | | 8/1998 | Cunningham |
| 5,800,392 A | | 9/1998 | Racchini |
| 5,800,408 A | | 9/1998 | Strauss et al. |
| 5,840,701 A | | 11/1998 | Hsia |
| 5,861,175 A | | 1/1999 | Walters et al. |
| 5,868,674 A | | 2/1999 | Glowinski et al. |
| 5,908,407 A | | 6/1999 | Frazee et al. |
| 5,964,705 A | * | 10/1999 | Truwit et al. ............... 600/423 |
| 6,026,316 A | * | 2/2000 | Kucharczyk et al. ....... 600/420 |
| 6,061,587 A | * | 5/2000 | Kucharczyk et al. ....... 600/411 |
| 6,560,475 B1 | * | 5/2003 | Viswanathan ............... 600/410 |
| 6,587,706 B1 | * | 7/2003 | Viswanathan ............... 600/410 |

FOREIGN PATENT DOCUMENTS

| | | |
|---|---|---|
| JP | 4008342 | 1/1992 |
| WO | 93/15784 | 8/1993 |
| WO | 93/15785 | 8/1993 |
| WO | 93/15872 | 8/1993 |
| WO | 93/15874 | 8/1993 |
| WO | 94/27697 | 12/1994 |
| WO | 96/33761 | 10/1996 |

OTHER PUBLICATIONS

Bouvier, G., et al., "Direct Delivery of Medication into a Brain Tumor through Multiple Chronically Implanted Cathethers", *Neurosurgery*, 20 (2), pp. 286-291, (Feb. 1987).

Broaddus, W.C., et al., "Distribution and stability of antisense phosphorothioate oligonucleotides in rodent brain following direct intraparenchymal controlled-rate infusion", *Journal of Neurosurgery*, 88 (4), pp. 734-742, (Apr. 1998).

Cares, H.L., et al., "Laboratory experience with a magnetically guided intravascular catheter system", *Journal of Neurosurgery*, 38 (2), pp. 145-154, (Feb. 1973).

Chandler, W.F., et al., "Use of Implantable Pump Systems for Intraarterial, Intraventricular and Intratumoral Treatment of Malignant Brain Tumors", *Annals of the New York Acadamy of Sciences*, 531, Neurological Applications of Implanted Drug Pumps, Edited by R.D. Penn, pp. 206-212, (1988).

Coutts, G.A., et al., "Integrated position tracking and imaging of interventional tools and internal devices using small fiducial receiver coils", *Proceedings of the International Society for Magnetic Resonance in Medicine, Fifth Scientific Meeting and Exhibition*, vol. 3, Vancouver, BC, Canada, p. 1924, (Apr. 12-18, 1997).

Driller, J., et al., "A review of medical applications of magnet attraction and detection", *Journal of Medical Engineering & Technology*, 11 (6), pp. 271-277, (Nov./Dec. 1987).

Dubach, M., "Accurate stereotaxic injection by radially curved injection needles", *Neurosurgery*, 29 (1), pp. 144-149, (Jul. 1991).

Erhart, P., et al., "Tissue-independent tracking of biopsy needles with an internal signal source", *Proceedings of the International Society for Magnetic Resonance in Medicine*, Fourth Scientific Meeting and Exhibition, vol. 3, New York, USA, p. 1740, (1996).

Gillies, G., et al., "Magnetic Manipulation Instrumentation for Medical Physics Research", *Review of Scientific Instruments*, 65 (3), Review Article, pp. 533-562, (Mar. 1994).

Ghöde, S.C., et al., "MR-Guided Cholecystostomy in a Pig: Assessment of biplanar, real-time Needle Tracking", *Proceedings of the International Society for Magnetic Resonance in Medicine, Fourth Scientific Meeting and Exhibition*, vol. 2, New York, USA, p. 892, (1996).

Grady, M., et al., "Magnetic Stereotaxis: A Technique to Deliver Stereotactic Hyperthermia", *Neurosurgery*, 27 (6), Technical Note, pp. 1010-1016, (Dec. 1990).

Grady, M., et al., "Nonlinear Magnetic Stereotaxis: Three-Dimensional, in vivo Remote Magnetic Manipulation of a Small Object in Canine Brain", *Medical Physics* 17 (3), pp. 405-415, (May/Jun. 1990).

Grady, M., et al., "Preliminary Experimental Investigation of in vivo Magnetic Manipulation: Results and Potential Application in Hyperthermia", *Medical Physics*, 16 (2), pp. 263-272, (Mar./Apr. 1989).

Hajnal, J.V., et al., "MR Imaging of Anisotropically Restricted Diffusion of Water in the Nervous System: Technical, Anatomic, and Pathologic Considerations", *Journal of Computer Assisted Tomography*, 15 (1), pp. 1-18, (Jan./Feb. 1991).

Hasegawa, Y., et al., "Temperature dependent change of apparent diffusion coefficient of water in normal and ischemic brain of rats", *Journal of Cereberal Blood Flow and Metabolism*, 14 (3), pp. 383-390, (1994).

Hilal, S.K., et al., "Magnetically guided devices for vascular exploration and treatment", *Radiology*, 113 (3), pp. 529-540, (Dec. 1974).

Hilal, S.K., et al., "POD Catheter: A Means for Small Vessel Exploration", *Abstract, Journal of Applied Physics 40* (3), p. 1046, (Mar. 1, 1969).

Howard, M., et al., "Magnetic Movement of a Brain Thermoceptor", *Neurosurgery*, 24 (3), pp. 444-448, (1989).

Howard, M.A., "Stereotaxic pallidotomy for the treatment of Parkinson's Disease", *Current Surgery*, 54 (1), pp. 31-34, (Jan. 1997).

Howard, M.A., et al., "An integrated multipurpose lesion-making electrode", *Neurosurgery*, 42 (1), pp. 137-142, (Jan. 1998).

Howard, M.A., et al., "Magnetically guided sterotaxis", *In: Advanced Neurosurgical Navigation*, Chapter 45, Edited by E. Alexander III et al., Thieme Medical Publishers, Inc., New York, pp. 549-556, (1999).

Hurst, G.C., et al., "Intravascular (Catheter) NMR Receiver Probe: Preliminary Design Analysis and Application to Canine Iliofemoral Imaging", *Magnetic Resonance in Medicine 24* (2), pp. 343-357, (Apr. 1992).

Johnston, J., et al., "Shiley Infusaid Pump Technology", *Annals of the New York Academy of Sciences*, 531, Neurological Applications of Implanted Drug Pumps, pp. 57-65, (1988).

Kucharczyk, J., et al., "Differential Effects of Brain Lesions on Thirst Induced by the Administration of Angiotensin-II to the Preoptic Region, Subfornical Organ and Anterior Third Ventricle", *Brain Research*, 108, pp. 327-337, (1976).

Laske, D.W., et al., "Chronic Interstital Infusion of Protein to Primate Brain: Determination of Drug Distribution and Clearance with Single-Photon Emission Computerized Tomography Imaging", *Journal of Neurosurgery 87* (4), pp. 586-594, (Oct. 1997).

Lieberman, D.M., et al., "Convection-enhanced distribution of large molecules in gray matter during interstitial drug infusion", *Journal of Neurosurgury*, 82 (6), pp. 1021-1029, (Jun. 1995).

Lux, H.D., et al., "The equilibration time course of $(K^+)_o$ in cat cortex", *Experimental Brain Research*, 17 (2), pp. 190-205, (Apr. 30, 1973).

Martin, A.J., et al., "MR Imaging of Blood Vessels with an Intravascular Coil", *Journal of Magnetic Resonance Imaging*, 2 (4), pp. 421-429, (Jul./Aug. 1992).

McNeil, R., et al., "Characteristics of an Improved Magnetic-Implant Guidance System", *IEEE Transactions on Biomedical Engineering*, 42 (8), pp. 802-808, (Aug. 1995).

McNeil, R., et al., "Functional Design Features and Initial Performance Characteristics of a Magnetic-Implant Guidance System for Stereotactic Neurosurgery", *IEEE Transactions on Biomedical Engineering*, 42 (8), pp. 793-801, (Aug. 1995).

Meeker, D., et al., "Optimal Realization of Arbitrary Forces in a Magnetic Stereotaxis System", *IEEE Transactions on Magnetics*, 32 (2), pp. 320-328, (Mar. 1996).

Molcho, J., et al., "Selective Cerebral Catheterization", *IEEE Transactions on Bio-Medical Engineering, BME-17*, (2), pp. 134-140, (Apr. 1970).

Molloy, J., et al., "Experimental Determination of the Force Required for Insertion of a Thermoseed into Deep Brain Tissues", *Annals of Biomedical Engineering*, 18, pp. 299-313, (1990).

Molloy, J., et al., "Thermodynamics of Movable Inductively Heated Seeds for the Treatment of Brain Tumors", *Medical Physics*, 18 (4), pp. 794-803, (Jul./Aug. 1991).

Morrison, P.F., et al., "High-Flow microinfusion: tissue penetration and pharmacodynamics", *American Journal of Physiology*, 266 (1) Part 2 of Two Parts, pp. R290-R305, (Jan. 1994).

Moseley, M.E., et al., "Anisotropy in diffusion-weighted MRI", *Magnetic Resonance in Medicine*, 19 (2), pp. 321-326, (Jun. 1991).

Moseley, M.E., et al., "Magnetic resonance imaging of diffusion and perfusion", *Topics in Magnetic Resonance Imaging*, (3), Magnetic Resonance Angiography, pp. 50-67, (Jun. 1991).

Netti, P.A., et al., "Time-dependent behavior for interstitial fluid pressure in solid tumors: implications for drug delivery", *Cancer Research*, 55 (22), pp. 5451-5458, (Nov. 15, 1995).

Nicholson, C., et al., "Diffusion from and iontophoretic point source in the brain: role of tortuosity and volume fraction", *Brain Research*, 169 (3), pp. 580-584, (Jun. 29, 1979).

Nicholson, C., et al., "Hindered diffusion of high molecular weight compounds in brain extracellular microenvironment measured with integrative optical imaging", *Biophysical Journal*, 65 (6), pp. 2277-2290, (Dec. 1993).

Nicholson, C., et al., "Ion diffusion modified by tortuosity and volume fraction in the extracellular microenvironment of the rat cerebellum", *The Journal of Physiology*, 321, pp. 225-257, (1981).

Oldendorf, W.H., "Speculations on the Instrumentation of the Nervous System", *Proceedings of the San Diego Symposium for Biomedical Engineering*, 2, San Diego, CA, pp. 274-280, (Jun. 19-21, 1962).

Penn, R.D., et al., "Intravascular intracranial EEG recording", *Journal of Neurosurgery*, 38 (2), Technical note, pp. 239-243, (Feb. 1973).

Prabhu, S.S., et al., "Distribution of macromolecular dyes in brain using positive pressure infusion: a model for direct controlled delivery of therapeutic agents", *Surgical Neurology*, 50 (4), pp. 367-375, (Oct. 1998).

Quate, E., et al., "Goniometric Motion Controller for the Superconducting Coil in a Magnetic Stereotaxis System", *IEEE Transactions on Biomedical Engineering*, 38 (9), pp. 899-905, (Sep. 1991).

Ram, W., et al., "Heart catheterization in a neonate by interacting magnetic fields: a new and simple method of catheter guidance", *Catheterization and Cardiovascular Diagnosis*, 22 (4), pp. 317-319, (Apr. 1991).

Ramos, P., et al., "Electro-Optic Imaging Chain for a Biplanar Fluoroscope for Neurosurgery: Magnetic Field Sensitivity and Contrast Measurements", *Optical Engineering*, 32 (7), pp. 1644-1656, (Jul. 1993).

Ramos, P., et al., "Microchannel Plate Image Intensifier Electron Dynamics in Magnetic Field", *Electronics Letters*, 27 (18), pp. 1636-1638, (Aug. 29, 1991).

Ritter, R.C., et al., "Measurement of friction on straight catheters in *in vitro* brain and phantom material", *IEEE Transactions on Biomedical Engineering*, 45 (4), pp. 476-485, (Apr. 1998).

Schmitt, F.O., "Molecular Regulators of Brain Function: A New View", *Neuroscience*, 13 (4), pp. 991-1001, (1984).

Sendelbeck, S.L., et al., "Spatial Distribution of Dopamine, Methotrexate and Antipyrine During Continuous Intracerebral Microperfusion", *Brain Research*, 328 (2), pp. 251-258, (Mar. 4, 1985).

Swanson, L.W., et al., "Autoradiographic Evidence for Pathways from the Medial Preoptic Area to the Midbrain Involved in the Drinking Response to Angiotensin II", *Journal of Comparative Neurology*, 178 (4), pp. 645-659, (Apr. 15, 1978).

Turner, R., "Minimum Inductane Coils", *J. Phys. E. Sci. Instrum*, 21, pp. 948-952, (1988).

Wimberger, D.M., et al., "Identification of "Premyelination" by Diffusion-Weighted MRI" *Journal of Computer Assisted Tomography*, 19 (1), pp. 28-33, (1995).

* cited by examiner

US 7,048,716 B1

MR-COMPATIBLE DEVICES

RELATED APPLICATIONS

This application is a continuation-in-part of U.S. patent application Ser. No. 09/131,031, filed Aug. 7, 1998, now U.S. Pat. No. 6,272,370, and is also a continuation-in-part of U.S. patent application Ser. No. 08/857,043, filed May 15, 1997, now U.S. Pat. No. 6,026,316.

BACKGROUND OF THE INVENTION

1. Field of the Invention

The present invention relates to a method of delivery of medical devices to patients, especially a method where (e.g., neurological) devices are delivered using nonlinear magnetic stereotaxis in conjunction with non-invasive MR imaging observation techniques such as magnetic resonance imaging, and most especially where drug delivery by said devices is accomplished under real time, non-invasive observation techniques such as magnetic resonance imaging which can indicate metabolic responses to the delivered drug and/or changes in soluble/dispersed concentrations of materials within liquids and/or tissue of a patient in real time or near real time. The present invention also generally relates to medical devices which are compatible with those and other procedures performed during magnetic resonance imaging (MRI), and particularly to medical devices which can deliver drugs during procedures viewed with magnetic resonance (MR) imaging techniques.

2. Background of the Prior Art

The concept of administering minimally invasive therapy and especially minimally invasive drug delivered therapy follows recent trends in medical and surgical practice towards increasing simplicity, safety, and therapeutic effectiveness. Image-guided, minimally invasive therapies have already superseded conventional surgical methods in several procedures. For example, transvascular coronary angioplasty is often now an alternative to open-heart surgery for coronary artery bypass, and laparascopic cholecystectomy is often an alternative to major abdominal surgery for gall bladder removal. The use of the less invasive techniques has typically reduced hospital stays by 1–2 weeks and the convalescence periods from 1–2 months to 1–2 weeks.

While endoscopic, arthroscopic, and endovascular therapies have already produced significant advances in health care, these techniques ultimately suffer from the same limitation. This limitation is that the accuracy of the procedure is "surface limited" by what the surgeon can either see through the device itself or otherwise visualize (as by optical fibers) during the course of the procedure. That is, the visually observable field of operation is quite small and limited to those surfaces (especially external surfaces of biological masses such as organs and other tissue) observable by visible radiation, due to the optical limitations of the viewing mechanism. MR imaging, by comparison, overcomes this limitation by enabling the physician or surgeon to non-invasively visualize tissue planes and structures (either in these planes or passing through them) beyond the surface of the tissue under direct evaluation. Moreover, MR imaging enables differentiation of normal from abnormal tissues, and it can display critical structures such as blood vessels in three dimensions. Prototype high-speed MR imagers which permit continuous real-time visualization of tissues during surgical and endovascular procedures have already been developed. MR-guided minimally invasive therapy is expected to substantially lower patient morbidity because of reduced post-procedure complications and pain. The use of this type of procedure will translate into shorter hospital stays, a reduced convalescence period before return to normal activities, and a generally higher quality of life for patients. The medical benefits and health care cost savings are likely to be very substantial.

A specific area where research is moving forward on advances of this type is in the treatment of neurological disorders. Specifically, the advent of new diagnostic and therapeutic technologies promises to extend the utility of intracerebral drug delivery procedures and thus possibly advance the efficacy of existing and/or planned treatments for various focal neurological disorders, neurovascular diseases and neurodegenerative processes. Currently, when the standard procedure requires neurosurgeons or interventional neuroradiologists to deliver drug therapy into the brain, the drug delivery device, such as a catheter, must either be passed directly through the intraparenchymal tissues to the targeted region of the brain, or guided through the vasculature until positioned properly. An important issue in either approach is the accuracy of the navigational process used to direct the movement of the drug delivery device. In many cases, the physical positioning of either part or all of the catheter's lumen within the brain is also important as, for example, in situations where a drug or some other therapeutic agent will be either infused or retroperfused into the brain through the wall or from the tip of the catheter or other drug delivery device.

New technologies like intra-operative magnetic resonance imaging and nonlinear magnetic stereotaxis, the latter discussed by G. T. Gillies, R. C. Ritter, W. C. Broaddus, M. S. Grady, M. A. Howard III, and R. G. McNeil, "Magnetic Manipulation Instrumentation for Medical Physics Research," *Review of Scientific Instruments*, Vol. 65, No. 3, pp. 533–562 (March 1994), as two examples, will likely play increasingly important roles here. In the former case, one type of MR unit is arranged in a "double-donut" configuration, in which the imaging coil is split axially into two components. Imaging studies of the patient are performed with this system while the surgeon is present in the axial gap and carrying out procedures on the patient. A second type of high-speed MR imaging system combines high-resolution MR imaging with conventional X-ray fluoroscopy and digital subtraction angiography (DSA) capability in a single hybrid unit. These new generations of MR scanners are able to provide the clinician with frequently updated images of the anatomical structures of interest, therefore making it possible to tailor a given interventional procedure to sudden or acute changes in either the anatomical or physiological properties of, e.g., a part of the brain into which a drug agent is being infused.

Nonlinear magnetic stereotaxis is the image-based magnetically guided movement of a small object directly through the bulk brain tissues or along tracts within the neurovasculature or elsewhere within the body. Electromagnets are used to magnetically steer the implant, giving (for example) the neurosurgeon or interventional neuroradiologist the ability to guide the object along a particular path of interest. (The implant might be either magnetically and/or mechanically advanced towards its target, but is magnetically steered, in either case. That is, magnetic fields and gradients are used to provide torques and linear forces to orient or shift the position of the implant or device, with a mechanical pushing force subsequently providing none, some, or all of the force that actually propels the implant or device. Additional force may be provided magnetically.) The implant's position is monitored by bi-planar fluoroscopy, and its location is indicated on a computerized atlas of brain images derived from a pre-operative MR scan. Among other applications, the implant might be used to tow a pliable catheter or other drug delivery device to a selected intracranial location through the brain parenchyma or via the neurovasculature. Magnetic manipulation of catheters and other probes is well documented in research literature. For example, Cares et al. (J. Neurosurg, 38:145, 1973) have described a magnetically guided microballoon released by RF induction heating, which was used to occlude experimental intracranial aneurysms. More recently, Kusunoki et al. (Neuroradiol 24: 127, 1982) described a magnetically controlled catheter with cranial balloon useful in treating experimental canine aneurysms. Ram and Meyer (Cathet. Cardiovas. Diag. 22:317, 1991) have described a permanent magnet-tipped polyurethane angiography catheter useful in cardiac interventions, in particular intraventricular catheterization in neonates.

U.S. Pat. No. 4,869,247 teaches the general method of intra parenchymal and other types of magnetic manipulation, and U.S. Pat. Nos. 5,125,888; 5,707,335; and 5,779,694 describe the use of nonlinear magnetic stereotaxis to maneuver a drug or other therapy delivery catheter system within the brain. U.S. Pat. No. 5,654,864 teaches a general method of controlling the operation of the multiple coils of a magnetic stereotaxis system for the purpose of maneuvering an implant to precisely specified locations within the body.

Both of these technologies offer a capability for performing image-guided placement of a catheter or other drug delivery device, thus allowing drug delivery directly into the brain via infusion through the walls of the catheter or out flow of the tip off the catheter. In the case of drug delivery directly into the brain tissues, the screening of large molecular weight substances by the endothelial blood-brain barrier can be overcome. In the case of infusions into specific parts of the cerebrovasculature, highly selective catheterizations can be enabled by these techniques. In either case, however, detailed visual images denoting the actual position of the drug delivery device within the brain would be extremely useful to the clinician in maximizing the safety and efficacy of the procedure. The availability of an MR-visible drug delivery device combined with MR-visible drug agents would make it possible to obtain near real-time information on drug delivery during interventional procedures guided by non-linear magnetic stereotaxis. Drug delivery devices, such as catheters, that are both MR-visible and radio-opaque could be monitored by two modalities of imaging, thus making intra-operative verification of catheter location possible during nonlinear magnetic stereotaxis procedures. (Intra-operative MR assessment might require the temporary removal of the magnetic tip of the drug delivery catheter and interruption of the magnetic stereotaxis procedure to image the patient.).

The geometry and magnetic strength of the magnetic tip will depend upon the particular type of catheter or medical device with which the tip is being used. In a preferred embodiment, the tip would have as small a maximum dimension as would be consistent with maintaining sufficient magnetic dipole moment to couple satisfactorily to the external magnetic fields and gradients used to apply torques and forces to the tip for the purpose of steering or moving the catheter or other medical device. It is preferred that the magnetic element (e.g., a distinct magnetic bead or seed or wire) or the magnetic tip have a maximum dimension of at least 0.5 mm, preferably from 0.5 to 8 mm, more preferably from about 1.0 to 6 mm, and most preferably from about 2 to 5 or 6 mm. To that end, the tip might be made of a permanently magnetic or magnetically permeable material, with compounds of Nd—B—Fe being exemplary, as well as various iron alloys (ferrites and steel alloys). The magnetic tip may be fixed to the distal end of the catheter in any number of ways, depending in part upon the method of use of the catheter, the specific type of catheter, the procedures and the use of the catheter. In one design, the magnetic tip might simply be a small spherical or oblate spheroid of magnetic material (e.g., having a geometry where the semi-major axis is from 1.1 to 3 times longer, preferably from 1.5 to 2.0 or 2.5 time longer than the semi-minor axis). The magnetic tip may be originally fixed to the distal end of the catheter or medical device or passed through the length of the catheter so that it abuts against the interal distal end of the catheter (as a foot would abut the end of a sock). As noted, the magnetic tip may be fixed in place either on the inside, outside or embedded within the composition of the distal end of the catheter or medical device. In a preferred embodiment, the magnetic tip may be thermally, solubly, mechanically, electronically or otherwise removably attached to and separable from the distal end of the catheter or medical device. A heat soluble link is taught in U.S. Pat. No. 5,125,888.

In still another embodiment, the magnetic tip would constitute a plug in the end of an otherwise open-ended catheter, and the tip might either have an open bore along its axis, a plurality of open bores along its axis, or a single or plural configuration of holes along the side of the magnetic tip, any of which openings would be used to facilitate drug delivery from the catheter or to serve as an exit port for the delivery of some other therapy or device into a body part, such as the parenchymal tissues and/or the cerebrobasculature of the brain. Alternatively, the magnetic tip might simply constitute a solid plug that seals the end of the catheter. The distal end of the catheter at which the magnetic tip is placed must be configured such that axial forces and torques applied by either magnetic fields and gradients or by a guide wire internal to the catheter allow said distal end and magnetic tip to be propelled towards a target site with the body, and to do so without said distal end and magnetic tip separating from each other in an inappropriate way and/or at an undesired time or under undesired circumstances. If the magnetic tip must be removed, or detached and removed, prior to MR imaging of the patient, such a procedure could be accomplished by the method taught in U.S. Pat. Nos. 5,125,888; 5,707,335; and 5,779,694, which call for dissolving a heat separable link between the tip and the catheter by a pulse of radio-frequency energy. An alternative means of removing the magnetic tip is discussed by M. A. Howard et al. in their article, "Magnetically Guided Stereotaxis," in Advanced Neurosurgical Navigation, edited by E. Alexander III and R. J. Maciunas (Thieme Medical Publisher, New York, 1998), which calls for withdrawing the magnetic tip from along the inside of the catheter that it has just steered into place within the body. Without removal of the magnetic tip from the catheter, whole body magnetic forces might be produced on it by the field of the MR imaging system, and these could cause undesired movement of the catheter that it has just steered into place within the body.

In the treatment of neurological diseases and disorders, targeted drug delivery can significantly improve therapeutic efficacy, while minimizing systemic side-effects of the drug therapy. Image-guided placement of the tip of a drug delivery catheter directly into specific regions of the brain can initially produce maximal drug concentration close to some targeted loci of tissue receptors following delivery of the drug. At the same time, the limited distribution of drug injected from a single catheter tip presents other problems. For example, the volume flow rate of drug delivery must be very low to avoid indiscriminate hydrodynamic damage or other damage to brain cells and nerve fibers. Delivery of a drug from a single point source may also limit the distribution of the drug by decreasing the effective radius of penetration of the drug agent into the surrounding tissue receptor population. Positive pressure infusion, i.e., convection-enhanced delivery of drugs into the brain, as taught by U.S. Pat. No. 5,720,720 may overcome the problem of effective radius of penetration. Also, U.S. patent application Ser. No. 08/857,043, filed on May 15, 1997 and titled "Method and Apparatus for Use with MR Imaging" describes a technology invented in-part by one of the present inventors comprising a method for observing the delivery of material to tissue in a living patient comprising the steps of a) observing by magnetic resonance imaging a visible image within an area or volume comprising tissue of said living patient, the area or volume including a material delivery device, b) delivering at least some material by the material delivery device into the area or volume comprising tissue of a living patient, and c) observing a change in property of said visible image of the area or volume comprising tissue of a living patient while said material delivery device is still present within the area or volume. This process, including the MRI visualization, is performed in approximately or actually real time, with the clinical procedure being guided by the MRI visualization.

Research on magnetic catheterization of cerebral blood vessels generally has focused on design of transvascular devices to thrombose aneurysms, to deliver cytotaxic drugs to tumors, and to deliver other therapies without the risks of major invasive surgery. Examples of such studies include Hilal et al (J. Appl. Phys. 40:1046, 1969), Molcho et al (IEEE Trans. Biomed. Eng. BME-17, 134, 1970), Penn et al (J. Neurosurg. 38:239, 1973), and Hilal et al (Radiology 113:529,1974).

U.S. Pat. Nos. 4,869,247, 5,654,864, 5,125,888, 5,707, 335 and 5,779,694 describe processes and apparatus for the use of magnetic stereotaxis for the manipulation of an object or implant which is moved into position within a patient, particularly within the cranial region and specifically within the brain but in principle elsewhere in the body also. These patents do no not involve any contemplation of real time visualization of drug distribution within the brain, especially by MRI. It should be noted that the potential exists for interactive interference between the two systems, magnetic resonance imaging and magnetic stereotaxis, particularly where fine images are being provided by a system based on magnetic coils, especially as described in U.S. patent application Ser. No. 08/916,596, filed on Aug. 22, 1997, which is incorporated herein by reference for its disclosure of the design, construction, structure and operation of coils and catheters in MR-guided procedures. That application describes medical devices which are compatible with procedures performed during magnetic resonance imaging (MRI), and particularly to medical devices which can deliver drugs during procedures viewed with magnetic resonance (MR) imaging techniques.

Medical procedures may now be performed on areas of the patient which are relatively small. Procedures may be performed on small clusters of cells, within veins and arteries, and in remote sections of the body with minimally invasive techniques, such as without surgical opening of the body. As these procedures, such as balloon angioplasty, microsurgery, electrotherapy, and drug delivery are performed within the patient with minimally invasive techniques without major surgical opening of the patient, techniques have had to be developed which allow for viewing of the procedure concurrent with the procedure. X-ray imaging, such as X-ray fluoroscopy, is a possible method of providing a view of the procedural area, but X-ray exposure for any extended period of time is itself harmful to the patient. Fiber optic viewing of the area does not provide any harmful radiation to the patient, but the fiber optics may take up too large a space to provide both the light necessary for viewing and a path for return of the light, and does not permit beyond the surface imaging (that is, only the surfaces of internal objects may be viewed from the position where the fiber optic device is located). Fiber optics or direct light viewing is more acceptable for larger area medical procedures such as gastroenterological procedures than for more microscopic procedures such as intraparenchymal drug delivery or endovascular drug delivery or procedures.

Techniques have been developed for relatively larger area viewing of MR-compatible devices within a patient by the use of MR-receiver coils in the devices which are tracked by MR imaging systems. Little by way of specific design considerations have been given to devices which have MR viewing capability and specific treatment functions, and especially where the relationship of specific types of treatment and the MR receiver coils must be optimized both for a treatment process and for MR viewing ability.

U.S. Pat. No. 5,211,165 describes a tracking system to follow the position and orientation of an invasive device, and especially a medical device such as a catheter, using radio frequency field gradients. Detection of radio frequency signals is accomplished with coils having sensitivity profiles which vary approximately linearly with position. The invasive device has a transmit coil attached near its end and is driven by a low power RF source to produce a dipole electromagnetic field that can be detected by an array of receive coils distributed around an area of interest of the subject. This system places the transmit coils within the subject and surrounds the subject with receive coils.

U.S. Pat. No. 5,271,400 describes a tracking system to monitor the position and orientation of an invasive device within a subject. The device has an MR active sample and a receiver coil which is sensitive to magnetic resonance signals generated by the MR active sample. These signals are detected in the presence of magnetic field gradients and thus have frequencies which are substantially proportional to the location of the coil along the direction of the applied gradient. Signals are detected responsive to sequentially applied mutually orthogonal magnetic gradients to determine the device's position in several dimensions. The invasive devices shown in FIGS. 2a and 2b and rf coil and an MR active sample incorporated into a medical device and an MR active sample incorporated into a medical device, respectively.

U.S. Pat. No. 5,375,596 describes a method and apparatus for determining the position of devices such as catheters, tubes, placement guidewires and implantable ports within biological tissue. The devices may contain a transmitter/detector unit having an alternating current radio-frequency transmitter with antenna and a radio signal transmitter situated long the full length of the device. The antennae are connected by a removable clip to a wide band radio frequency (RF) detection circuit, situated within the transmitter/detector unit.

U.S. Pat. No. 4,572,198 describes a catheter for use with NMR imaging systems, the catheter including a coil winding for exciting a weak magnetic field at the tip of the catheter. A loop connecting two conductors supports a dipole magnetic field which locally distorts the NMR image, providing an image cursor on the magnetic resonance imaging display.

U.S. Pat. No. 4,767,973 describes systems and methods for sensing and movement of an object in multiple degrees of freedom. The sensor system comprises at least one field-effect transistor having a geometric configuration selected to provide desired sensitivity.

Published PCT Applications WO 93/15872, WO 93/15874, WO 93/15785, and WO 94/27697 show methods of forming tubing, including kink resistant tubing and catheters in which the catheters may contain reinforcing coils. Layer(s) of reinforcing materials may be deposited on and over the reinforcing coils.

U.S. Pat. Nos. 5,451,774 and 5,270,485 describes a three-dimensional circuit structure including a plurality of elongate substrates positioned in parallel and in contact with each other. Electrical components are formed on the surfaces of the substrates, along with electrical conductors coupled to those components. The conductors are selectively positioned on each substrate so as to contact conductors on adjacent substrates. The conductor patterns on the substrates may be helical, circumferential, or longitudinal. Radio frequency signaling between substrates would be effected with a transmitting antenna and a receiving antenna, with radio frequency signal transmitting and receiving circuitry present in the substrates (e.g., column 7, lines 32–43). Circulation of cooling fluid within the device is shown.

U.S. Pat. No. 5,273,622 describes a system for the fabrication of microstructures (including electronic microcircuitry) and thin-film semiconductors on substrates, especially continuous processes for use on elongate substrates such as fibers or filaments.

U.S. Pat. Nos. 5,106,455 and 5,269,882 describes a method and apparatus for fabrication of thin film semiconductor devices using non-planar exposure beam lithography. Circuitry formed on cylindrical objects is shown.

U.S. Pat. No. 5,167,625 describes a multiple vesicle implantable drug delivery system which may contain an electrical circuit which is responsive to signals (including radio signals) which can be used to effect drug delivery.

PCT Application WO 96/33761 (filed 15 Apr. 1996) describes an intraparenchymal infusion catheter system for delivering drugs or other agents comprising a pump coupled to the catheter. A porous tip is disposed at a distal end of the catheter, the tip being porous to discharge an agent or dug at a selected site. The catheter may be customized during use by an expandable portion of the catheter system.

Martin, A. J., Plewes, D. B. and Henkelman, R. M. in "MR Imaging of Blood Vessels with an Intravascular Coil," J. Mag. Res. Imag., 1992, 2, No. 4, pp. 421–429 describes a method for producing high-resolution magnetic resonance (MR) images of blood vessel walls using a theoretic receiver-coil design based on two coaxial solenoids separated by a gap region and with the current driven in opposite directions. The coils had diameters ranging from 3 to 9 mm. FIG. 3b appears to indicate that sensitivity decreases as the coils diameter moved from 9 to 7 to 5 to 3 mm. Investigation of the Q value of opposed loop and opposed solenoid coils indicated that opposed loop coils displayed low W values and that there was a general trend of lower Q values at smaller Q diameters among the opposed solenoid designs. Within the range investigated, it was stated that a compromise exists between the use of thicker wire for improved performance and thinner wire to limit the overall coil dimensions. Decoupling circuitry is also shown to be useful in performing the imaging functions with this catheter based system in MR imaging.

Hurst, G. C., Hua, J., Duerk, J. I. and Choen, A. M., "Intravascular (Catheter) NMR Receiver Probe: Preliminary Design Analysis and Application in Canine Iliofemoral Imaging," Magn. Res. In Imaging, 24, 343–357 (1992) explores the feasibility of a catheter-based receiver probe for NMR study of arterial walls. Various potential designs, including opposed solenoids (e.g., FIG. 2b and FIG. 3 a and b) are examined. The catheter probe shown in FIG. 3 was constructed with five turns of 28 gauge wire per solenoid, with 7.5 mm between solenoids and nominal solenoid diameters of 2.8 mm, with the probe resonating at 64 MHz with a 110-pf capacitor.

A device is described for use within an organism, said device may comprise an element having at least one pair of opposed RF receiver microcoils having a space between each microcoil of said pair of microcoils, the coils of said microcoils having diameters of less than 2.4 mm. The device may comprise a catheter having at least one lumen, where the at least one pair of microcoils is radially located about the at least one lumen and the coils have diameters of greater than 0.1 mm and less than 2.4 mm. The device may have no ports or at least one drug delivery port present within said device. The least one drug delivery port may be located so that at least some drug which is delivered through said port is delivered away from said device within said space between said microcoils. The delivery ports may comprise microcatheters present within said device which extend outside of said device to deliver at least some liquid material within a volume bordered by planes extending radially from the catheter at ends of the at least one pair of microcoils which define the space between each microcoil within said at least one pair of microcoils. The device, in response to radio frequency transmission, may generate a field which has an average strength within said volume than in comparable size volumes surrounding said catheter which are radially located directly over each of said microcoils. The at least one pair of microcoils preferably is embedded within a binder material which surrounds said lumen. The at least one pair of microcoils is electrically connected to a preamplifier within a portion of said device which may be inserted into an organism. Where electrical connections are present within said device, it is preferred that at least some of said electrical connections have been formed in situ within said device.

This invention provides a method and object for selective intraparenchymal and/or neuroendovascular drug delivery and other concurrent medical treatment of abnormalities of the human central nervous system concurrent with nonlinear magnetic stereotaxis combined with magnetic resonance (MR) imaging and/or x-ray guidance.

Magnetic Resonance Imaging (MRI) is used in combination with 1) an MR observable delivery device or 2) an MR observable medical device which can alter a water based molecular environment by performed medical operations, the delivery device or medical device being used in the presence of MR observable (in water, body fluid or tissue) compound(s) or composition(s). MRI images are viewed with respect to a molecular environment to determine the position of the delivery device or medical device (hereinafter collectively referred to as the "delivery device" unless otherwise specifically identified) and changes in the environment where the delivery device is present as an indication of changes in the molecular environment. As the delivery of material from the delivery device is the most MR visible event within the molecular environment in the vicinity of the delivery area, the changes in the molecular environment are attributable to the delivery of the MR observable compounds or compositions. Changes in signal properties, such as changes in the signal intensity within the MR images reflect the changes in the molecular environment and therefore track the location of delivered materials, and are indicative of delivery rates and delivery volumes in viewable locations. With the medical device, chemical composition within the molecular environment may also be altered as by the removal of deposits of certain materials into the liquid (water) environment or stimulated activity of tissue to release materials, where those materials can alter the MR response. Some materials that may be removed by medical procedures will not affect the MR response, such as calcium, but fatty materials may affect the response. Additionally, medical treatments which stimulate natural activities of chemical producing systems (e.g., the glands, organs and cells of the body which generate chemicals such as enzymes and other chemicals with specific biological activity [e.g., dopamine, insulin, etc.]) can be viewed under direct MR observation and any changes in chemical synthetic activity and/or delivery can be observed because of molecular environment changes which occur upon increased synthetic activity.

One recently established method of reading the data obtained from the MR imaging is technically founded upon existing knowledge of Apparent Diffusion Coefficients (ADC) in particular regions of the body. There is significant published literature with respect to ADC values for specific tissues in various parts of animals, including various tissues of humans (e.g., Joseph V. Hajnal, Mark Doran, et al., "MR Imaging of Anisotropically Restricted Diffusion of Water in the Nervous System: Technical, Anatomic, and Pathological Considerations," Journal of Computer Assisted Tomography, 15(I): 1–18, January/February, 1991, pp. 1–18). It is also well established in the literature that loss of tissue structure through disease results in a decrease of the ADC, as the tissue becomes more like a homogeneous suspension. Clinical observations of changes in diffusion behavior have been made in various tissue cancers, multiple sclerosis, in strokes (where the reduction in diffusion precedes the increase in T2), and in epilepsy. (e.g., Y. Hasegawa, L. Latour, et al. "Temperature Dependent Change of Apparent Diffusion Coefficient of Water in Normal Ischemic Brain", Journal of Cerebral Blood Flow and Metabolism 14:389–390, 1994). Thus, ADC values are specific for specific types of tissues. Accordingly, as different drugs/chemicals are introduced into a tissue volume under MR observation, the change in ADC resulting from each drug/chemical interaction with the ambient water proton environment can be observed.

While the ADC is the preferred means within the present invention of mapping the delivery of drug in tissue, other embodiments of the invention allow for additional tissue contrast parameters to track the delivery of a drug into tissue. In other words, the delivery of a drug into tissue will cause other MRI-observable changes which can be mapped (as is done for ADC) and which can be used to map the spatial distribution characteristics of the drug within and around the targeted tissue. While some of these observations may be larger in magnitude than others, any of the MRI contrast mechanisms' effects can be used as a tracking mechanism to longitudinally evaluate the spatial kinetics of drug movement within the imaging volume.

The tissue contrast changes apparent on an MR image can arise from ADC, from alterations in the BO magnetic field (often referred to as magnetic susceptibility or ABO produced by the presence of a substance in said tissue), from alterations in local tissue T1 relaxation times, from local T2 relaxation times, from T2* relaxation times (which can be created by susceptibility differences), from the magnetization transfer coefficients (MTC is an effect produced by local communication between free water protons and those of nearby macromolecular structures), from the ADC anisotropy observed in oriented matter, and also from local differences in temperature which will affect in varying degrees all of the included tissue contrast parameters. In addition, the delivery of drug can also be tracked from magnetic field frequency shifts caused by the drug or arising from agents (e.g., MR taggants) added with unique frequency shifts from those of the local protons (such as that created from F-19 or fluorine-19 agents found in or added to the drug).

MR imaging of the alterations in the BO magnetic field (also known as imaging of the local magnetic susceptibility) can reveal the spatial distribution of a drug from the interaction of the drug with the otherwise homogeneous magnetic field found in MRI. To enhance the alterations in the magnetic field BO caused by the drug, small amounts of a BO-altering added agent or agents can be added to the drug during delivery. This can include iron oxide particles, or other materials, such as those comprising lanthanide-, manganese-, and iron-chelates. In addition, vehicles containing differing gases ($N_2$, $O_2$, $CO_2$) will also alter the local magnetic field and thus produce a magnetic susceptibility effect which can be imaged.

The invention includes a device for use in conjunction with magnetic stereotaxis guidance and device delivery and a method for MR-guided targeted drug delivery into a patient, such as intracranial drug delivery, intraspinal drug delivery, intrarenal drug delivery, intracardial drug delivery, etc. The MR-visible drug delivery device is guided by magnetic stereotaxis to the target tissue and/or advanced within entrance points to the patient such as periventricular, intracerebroventricular, subarachnoid, intraparenchymal tissues or the cerebrovasculature under magnetic resonance imaging or real time X-ray fluoroscopy, and all of this is possibly also done in conjunction with conventional methods of neurosurgical or neuroradiologic catheter manipulation. The drug delivery device preferably has a linearly arranged array of radiopaque and MR-visible markers disposed at its distal end to provide easily identifiable reference points for trackability and localization under susceptibility MR imaging and X-ray fluoroscopy guidance. Additionally, active MR visualization of the drug delivery device is achieved or enhanced by means of RF microcoils positioned along the distal axis of the device. MR visibility can be variably adjustable based on requirements related to degree of signal intensity change for device localization and positioning, enhancement along the shaft of the device, enhancement around the body of the device, visibility of the proximal and distal ends of the device, degree of increased background noise associated with device movement, and other factors which either increase or suppress background noise associated with the device. Since the tip of the drug delivery device can be seen on MR and X-ray images and thus localized within the brain, the multiple point source locations of drug delivery are therefore known and can be seen relative to the tip or the shaft of the device.

Targeted delivery of drug agents may be performed by any therapeutically effective drug delivery device or system, including, for example, those utilizing MR-compatible pumps connected to variable-length concentric MR-visible dialysis probes each with a variable molecular weight cut-off membrane, or by another MR-compatible infusion device which injects or infuses a diagnostic or therapeutic drug solution. Imaging of the injected or infused drug agent is performed by MR diffusion mapping using the RF microcoils attached to the distal shaft of the injection device, or by imaging an MR-visible contrast agent that is injected or infused through the walls of the dialysis fiber into the brain. The delivery and distribution kinetics of injections or infusions of drug agents at rates, for example, of between 1 μl/min (or less) to 1000 μl/min (or more) are monitored quantitatively and non-invasively using real-time contrast-enhanced magnetic susceptibility MR imaging combined with water proton directional diffusion MR imaging. One aspect of the present invention is to provide a non-invasive, radiation-free imaging system for tracking a drug delivery or other medical device to a target intracranial location in conjunction with or following magnetic stereotaxis manipulation and placement of the drug delivery device in the procedure.

Another aspect of the present invention is to provide an imaging system for visualizing the distal tip of the drug delivery or other medical device at the target intracranial location in conjunction with or following magnetic stereotaxis delivery of the drug delivery device in the procedure.

A third aspect of this invention is to provide for an MR-compatible and visible device that significantly improves the efficacy and safety of intracranial drug delivery using MR guidance in conjunction with or following magnetic stereotaxis delivery of the drug delivery device in the procedure.

A fourth aspect of the present invention is to provide for interactive MR imaging of injected or infused MR-visible drug agents superimposed upon diagnostic MR images of the local intracranial anatomy in conjunction with or following magnetic stereotaxis delivery of the drug delivery device and manipulation and placement of the device in the procedure.

A fifth aspect of the present invention is provide an MR imaging method for quantitative monitoring of the spatial distribution kinetics of a drug agent injected or infused from a drug delivery device into the central nervous system or cerebrovascular system to determine the efficacy of drug delivery at various sites, such as at intracranial target sites.

A sixth aspect of the present invention is to provide for magnetically responsive catheters and other drug delivery devices which can be steered by an applied magnetic field using nonlinear magnetic stereotaxis to provide directional control of the tip of the device to guide the device to targeted intracranial locations.

A seventh aspect of this invention is to provide for a magnetically responsive catheter device which can be steered or navigated through bulk tissues in the brain using nonlinear magnetic stereotaxis with minimal frictional drag and minimal tissue injury.

An eighth aspect of this invention is to provide for a magnetically responsive catheter device which can be guided by nonlinear magnetic stereotaxis to sites of cerebrovascular lesions, including aneurysms, stroke sites, tumors, arteriovenous malformations and fistulae.

A ninth aspect of the present invention is to provide an MR imaging method to evaluate how the spatial distribution kinetics of a drug agent injected or infused from a drug delivery device into the central nervous system is influenced by infusion pressure, flow rate, tissue swelling and other material properties of the brain, and by the physicochemical and pharmaco kinetics nature of the drug or therapeutic agent infused.

BRIEF DESCRIPTION OF THE DRAWINGS

FIG. 3 is a view of another embodiment of the device according to the present invention. The view shows the disposition of microcoil elements at the distal tip of the drug delivery device.

FIG. 1 shows a drug delivery catheter according to a practice of the present invention.

FIG. 2 shows a sectional view of a catheter emphasizing microcatheter exits on the catheter and wiring on the catheter.

FIGS. 4a, b, and c shows graphic respresentations of Field Strength versus distance from the center of the gap between two opposed pairs of microcoils for three microcoil structures.

DETAILED DESCRIPTION OF THE INVENTION

Figure 1:
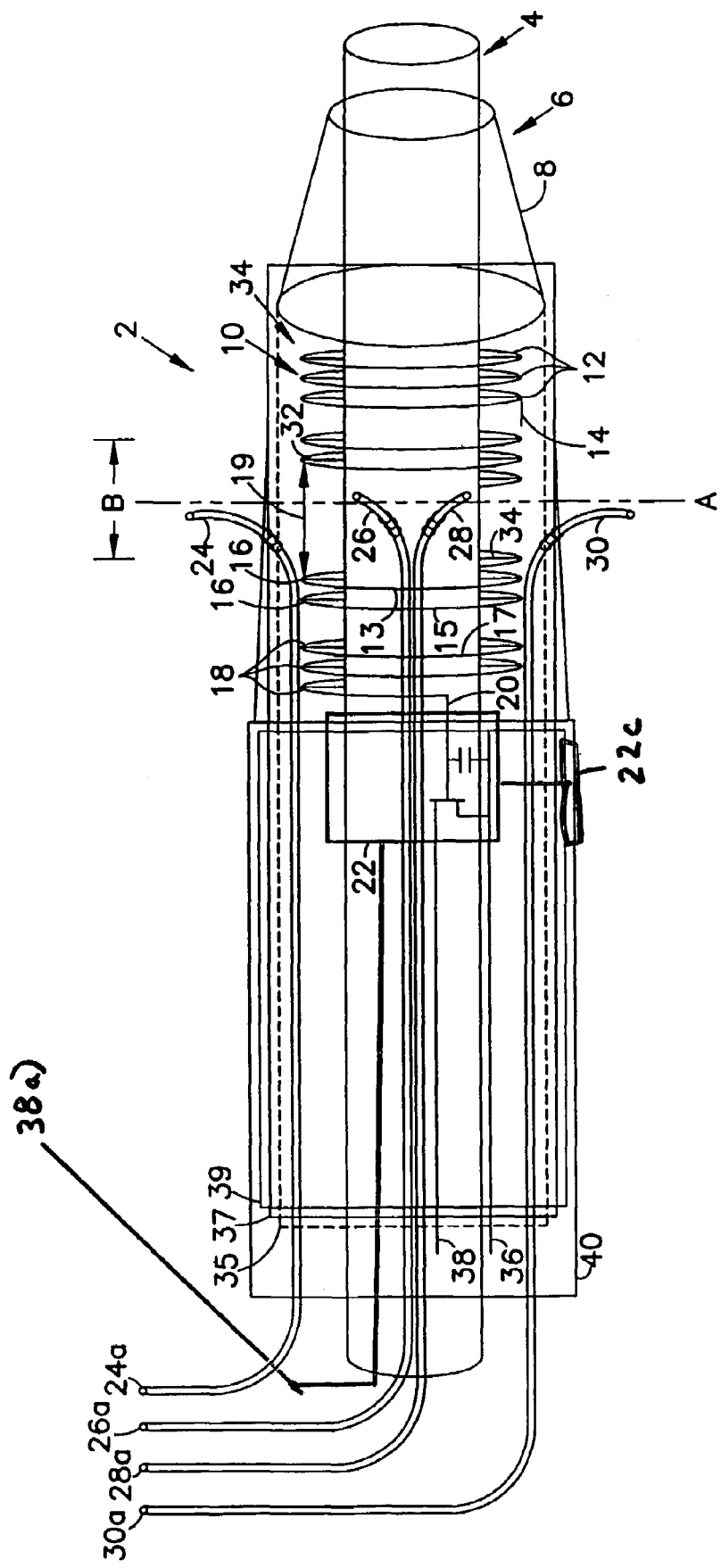
FIG. 1 is a side elevational view, partially in cross-section, of a retroperfusion microcatheter or other drug delivery device which might be used for infusion, retroperfusion or other purposes according to one embodiment of the present invention, that is designed to be maneuvered intracranially via nonlinear magnetic stereotaxis. The view shows the disposition of radio-opaque and MR markers, and the relationship of the osmotic pump and microdialysis probe.

In the following detailed description of the preferred embodiments, references made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical, physical, architectural, and electrical changes may be made without departing from the spirit and scope of the present invention. The following detailed description is, therefore, not to be taken in a limiting sense, and the scope of the present invention is defined only by the appended claims and their equivalents.

The practice of certain aspects of the present invention are applicable to all medical devices which might be used with magnetic resonance imaging viewing procedures occurring concurrently with the primary medical procedure. Features of the present invention which may individually have this general applicability within the medical device field include the types of RF-responsive coils provided to medical devices to assure their MR-compatibility, circuitry associated with the devices, and means for directing microelements/microcatheter components and the like within a catheter device. The preferred construction uses an opposed solenoid orientation of microcoils with the microcoil design based on two coaxial solenoids separated by a gap region and with the current driven in opposite directions across the two coils.

One individual aspect of the present invention is the use of an opposed pair(s) of microcoils to accurately define a field around the device carrying the pair(s) of coils. By an opposed pair of coils is meant coils in which the angle of their coiling or winding about an axis is different (in a positive or negative sense, either with positive degree rotation away from a line perpendicular to the surface or negative degree rotation away from the line) between two sets of coils (e.g., receiver coils), usually with the angles differing from a plane perpendicular to the axis of the object about which the coils are wound or formed by +degrees for one coil and −degrees for the other coil as measured from the plane. Other individual advances in the potential areas of practice of the present invention include the circuitry which is connected to the coils, its shielding within the device, and decoupling circuitry associated with the wires to the coils. Little specificity has heretofore been provided within the actual design and engineering details of radio frequency detectable invasive medical devices which addresses a wide range of functional needs within the device. This invention provides a substantive advance in the design of such devices.

Another area of import to the present invention is the option of providing drug delivery microcatheters within the radio frequency detectable device, with the receiver coils being usable in a process for detecting the actual delivery and movement of drugs according to the invention described in copending U.S. patent application Ser. No. 08/916,596 filed on Jun. 22, 1997 in the names of John Kucharczyk and Michael Moseley.

FIG. 1 shows a preferred drug delivery catheter 2 according to the present invention. The catheter 2 comprises a central lumen 4 which exits through a port 6 in a tapered end 8 of the catheter 2. A first microcoil 10 is wrapped about the lumen 4 so that the individual coils 12 generally angle away from the tapered end 8. A lead wire 14 is connected to the first microcoil 12. A second microcoil 16 is wrapped about the lumen 4 and the individual coils 18 are generally angled towards the tapered end 8. This pair of first microcoil 10 (and 32, collectively referred to as 10) and second microcoil 16 (and 18, collectively referred to as 16) form an opposed pair of microcoils. The individual coils of 10 and 32 for the relatively proximal set of microcoils 10 and the individual coils 16 and 18 for the second microcoil 16 have opposite (positive versus negative) angles with respect to a plane A-B which would be perpendicular to the lumen 4, which effectively defines an axis for the catheter 2. Note that the pair of coils may have different spacing between adjacent coils, e.g., between 13 and 15, as compared top between 15 and 17). This difference in spacing will be discussed later. A lead wire 20 passes from the second microcoil 16 to electronic circuitry 22, as does the lead wire 14 from the first microcoil 10. There is a definite separation of space between the first microcoil 10 and the second microcoil 16 within which the RF responsive field (not shown) from the coils 10 16 is the largest. It is within the space B outside of the catheter 2 in a zone defined by the opposed ends 32 34 of the two microcoils 10 16 (respectively) where delivery of drug from microcatheters 24, 26, 28 and 30 would be most effectively observed.

The microcoils 10 and 16 are embedded in a support material 34 which may be a polymeric material, composite material, inorganic material (e.g., inorganic oxide) or the like. The composition of this material should be biocompatable, preferably a polymeric material such as a polyamide, polyester, poly(meth)acrylate, polyvinyl acetate, cellulose acetate, or other classes of organic polymers which are biocompatable. This support material 34 may also comprise the composition of the tapered end 8. Lead wires 36 and 38 leave the circuitry 22 for connections to outside controls and/or power sources. The ends 24a, 26a, 28a, and 30a of the microcatheters 24, 26, 28 and 30 are shown, without their connection to a delivery system or pump for provision of agents or drugs being shown.

The intermicrocoil spacing B (as opposed to the intramicrocoil spacing between the opposed sets of microcoils) will usually be optimized for each type of drug delivery or other type of procedure to be practiced by the MR-compatible device 2, whether a catheter or other device. The parameters which would be considered for optimization, particularly with respect to the location of the microcoils would include at least the diameter of the field from the coils which is desired, the strength of the field, the width of the field, the number of field locations (e.g., the number of pairs of opposed microcoils), the location of the pairs of microcoils with respect to the distal end of the catheter, the location of the microcoils with respect to the point of delivery of the agents or drugs, etc. These considerations would be in addition to such engineering and other design considerations such as the thickness and size of the coils, the composition of the coils, the location of the circuitry (within the catheter or connected to an external circuitry through leads), and the composition of the other materials within the catheter construction.

Within said catheter construction at the more proximal end (away from the tip) may be a plastic layer 35 (which here is shown as a continuation of layer 8), a second insulating (e.g., plastic, ceramic, or biocompatible material as with the previous description of the support material for in layer 34) layer 37 which covers and electrically insulates the leads (wires) 36 and 38, and any preamplifier which may be present associated with the microcoils, from the shielding 39 which may form a layer around (radially away from) the leads 36 and 38 and/or preamplifier.

Intracoil spacing and intramicrocoil considerations (which overlaps intercoil and intermicrocoil considerations, as with respect to coil diameters) should also be considered in optimizing the design of the systems of the present invention.

Coils, particularly coils such as intra-vascular RF coil in MRI, can be very useful for MR imaging of vascular lumen morphology at a reduced field of view (FOV) with a high signal to noise ratio and spatial resolution. The most promising fundamental coil design for this type of purpose is a previously published (Martin, supra) opposed solenoid coil. The reported coils are two uniformly wound solenoids of an identical geometry and uniform coil diameter placed along a common axis with a reversed polarity. That particular coil design leaves a lot of room for improvement, based upon considerations not disclosed in the reference. One basis for improvement of the functional characteristics of the signaling is that a better intra-vascular coil can be obtained with a proper optimization for the current distribution within the coils. To optimize the current distribution on the surface of the cylinder (e.g., assuming a cylindrical shape for the underlying device, such as the catheter) with respect to a set of required field constraints, an analytical formulation for the magnetic field external to a cylindrical coil has been developed and is to be preferably used for our new coil design. Such an optimized coil yields an improved field strength and field uniformity. The uniform field strength is particularly important as certain methods of use of the devices of the invention use density readings and differentiations to generate the images or provide specific types pf information within the image (e.g., the rate of delivery of a drug or the degree of effect of a treatment represented by differences in signal density).

The geometry of the RF coil is, for the present analysis, based upon a small cylinder of a finite length. The current density is confined on the surface of the cylinder in the coils. Solving an appropriate static magnetic field problem for the geometry, for a cylindrical shaped coil of radius a, the radial components of the magnetic field outside of the RF coil (>a) is given as $$B_r(\rho, z, \phi) = i\frac{\mu_0 a}{2\pi} \sum_{m=-\infty}^{m=+\infty} \int_{-\infty}^{+\infty} J_\phi(m, k) kK'_m(ka) I'_m k\rho \Big) e^{+i(kz+m\phi)} dk$$

where $J_\phi(m,k)$ denotes the azimuthal component of the surface current density in the expression above defined as $$J_\phi(m, k) = \frac{1}{2\pi} \int_0^{2\pi} d\phi e^{im\phi} \int_{-\infty}^{+\infty} dz J_\phi(\phi, z) e^{ikz}$$

and $I_m(t)$ and $K_m(t)$ denote two kinds of modified Bessel functions, of $m^{th}$ order, wherein m denotes an integer (e.g., 1, 2, 3 . . . ), and $I'_m(t)$ and $K'_m(t)$ represent a first derivative of $I_m(t)$ and $K_m(t)$ with respect to t.

The stored magnetic energy associated with the coil is found and given analytically in a form of series expansion as $$W = \frac{-\mu_0 a^2}{2} \sum_{m=-\infty}^{+\infty} \int_{-\infty}^{+\infty} |J_\phi(m, k)|^2 K'_m(ka) I'_m(ka) dk$$

Specifically for a solenoid coil or a z-coil in which the surface current density has no z-component, these expressions for both energy and field are simplified as:

$$W = \frac{-\mu_0 a^2}{2} \int_{-\infty}^{+\infty} |J_\phi(0, k)|^2 K'_0(ka) I'_0(ka) dk -$$

$$B_r(\rho, z, \phi) = i\frac{\mu_0 a}{2\pi} \int_{-\infty}^{+\infty} J_\phi(0, k) kK'_0(k\rho) I'_0(ka) e^{+ikz} dk$$

To seek an optimal (or energy minimum) solution for current density distribution on the surface of the cylinder satisfying a set of the field constraints at some spatial locations, an energy functional construction is defined as follows, $$F = W - \sum_j \lambda_j (B_\rho(r_j) - B_j)$$

$$= \frac{-\mu_0 a^2}{2} \int_{-\infty}^{+\infty} |J_\phi(0, k)|^2 K'_0(ka) I'_0(ka) dk -$$

$$\sum_j \lambda_j \Big[ i\frac{\mu_0 a}{2\pi} \int_{-\infty}^{+\infty} J_\phi(0, k) kK'_0(k\rho_j) I'_0(ka) e^{+ikz_j} dk B_j \Big]$$

where represents a set of L multipliers. The field constraints specify a set of desired field values at a few points over an imaging volume of interest.

Minimizing the energy functional with respect to the current density functional, the variation to respect to the current density functional is performed:

$$\frac{\delta F}{\delta J} = \frac{\delta W}{\delta \delta J} - \sum_j \lambda_j \frac{\delta B_\rho(r_j)}{\delta J}$$

$$= \frac{\mu_0 a^2}{2} 2 J_\phi(0, k) K'_0(ka) I'_0(ka) - \sum_j \lambda_j i\frac{\mu_0 a}{2\pi} kK'_0(k\rho_j) I'_0(ka) e^{+ikz_j}$$

Then, the optimized current density is expressed in terms of the L multipliers as, $$J_\phi(0, k) = -i\sum_j \lambda_j \frac{k}{2\pi a} \frac{K'_0(k\rho_j)}{K'_0(ka)} e^{+ikz_j}$$

Since $J_\phi(z)$ will be antisymmetric in z for the desired field distribution, then its Fourier component can be expressed as $$J_\phi(0, k) = i\int_{-\infty}^{+\infty} dz J_\phi(0, z) \sin(kz)$$

Inserting the expression for current density into the field constraint equations, a set of linear equation for the multipliers λ can be obtained:

$$B_{\rho n} = \frac{\mu_0}{4\pi^2} \sum_n \lambda_n \int_{-\infty}^{+\infty} \cos(kz_m)\cos(kz_n) \frac{K'_0(k\rho_n)}{K'_0(ka)} kK'_0(k\rho_m) I'_0(ka) dk$$

Solving the linear field constraint equations for the Langrange multipliers, then the current density can be determined from the expression involving these Langrange multipliers. For an RF coil of finite length (L), the surface current density can be expanded in terms of a sine series to a desired order, $$J_\phi(z) = \sum_{n=0} J_n \sin\left(\frac{2n\pi z}{L}\right) = \sum_{n=1}^N J_n \sin(k_n z)$$

$$J_\phi(k) = i\int_{-\infty}^{+\infty} dz J_\phi(z) \sin(kz)$$

where the value of $k_n$ is $$k_n = \frac{2\pi n}{L}$$

wherein n is an integer (e.g., n=1, 2, 3, 4 . . . ) and $J_n$ denotes a set of expansion coefficients for the current density.

Then the general expression in k-space for the surface current density for the finite length coil can be written as:

$$J_\phi(k) = \int_{-\infty}^{+\infty} dz \sum_{n=0} J_n \sin\left(\frac{2n\pi z}{L}\right) e^{ikz}$$

$$= \frac{L}{2} \sum_{n=0} J_n \Psi_n(k)$$

where $\Psi_n(k)$ is an odd function in k, which is defined as $$\Psi_n(k) = \frac{\sin[(k+k_n)L/2]}{[(k+k_n)L/2]} - \frac{\sin[(k-k_n)L/2]}{[(k-k_n)L/2]}$$

Using the new function expansion, the corresponding expressions for stored magnetic energy and field can be written as $$W = \frac{\mu_0 a^2}{2} \int_{-\infty}^{+\infty} \left|\frac{L}{2} \sum_{n=0} J_n \Psi_n(k)\right|^2 K_0'(ka) I_0'(ka) dk$$

$$= \frac{\mu_0 a^2}{2}\left(\frac{L}{2}\right)^2 \sum_{m,n=0} J_m J_n \int_{-\infty}^{+\infty} \Psi_m(k)\Psi_n(k) K_0'(ka) I_0'(ka) dk$$

$$B_r(\rho, z, \phi) = \frac{\mu_0 a}{2\pi}\left(\frac{L}{2}\right) \sum_n J_n \int_{-\infty}^{+\infty} \Psi_n(k) k K_0'(k\rho) I_0'(ka) \cos(kz) dk$$

The desired reception field distribution external to a coil can be translated into a few field constraint points at some selected locations. For each particular design, these field constraint points are defined as:

z=0.000 ρ=r $B_\rho$=1.0
z=0.005 ρ=r $B_\rho$=0.8

The constraints specify a required field homogeneity of the coil at the gap as well as the relative field strength. The field constraint equations for radial component at various points of interests can be represented as follows $$B_r(\rho_j, z_j) = \sum_n J_n b_{nj}$$

$$= \frac{\mu_0 a}{2\pi}\left(\frac{L}{2}\right) \sum_n J_n \int_{-\infty}^{+\infty} \Psi_n(k) k K_0'(k\rho_j) I_0'(ka) \cos(kz_j) dk$$

For convenience, both field and energy expressions are expressed in matrix form. Among the two, the matrix elements for b are given as $$b_{nj} = \frac{\mu_0 a}{2\pi}\left(\frac{L}{2}\right) \int_{-\infty}^{+\infty} \Psi_n(k) k K_0'(k\rho_j) I_0'(ka) \cos(kz_j) dk$$

The magnetic stored energy in the coil is $$W = \frac{-1}{2}\mu_0 a \left(\frac{L}{2}\right)^2 \sum_{mn} J_m J_n \int_{-\infty}^{+\infty} \Psi_m(k)\Psi_n(k) K_0'(ka) I_0'(ka) dk$$

$$= \frac{1}{2} \sum_{mn} J_m J_n W_{mn}$$

where the energy matrix elements are given by $$W_{mn} = -\mu_0 a \left(\frac{L}{2}\right)^2 \int_{-\infty}^{+\infty} \Psi_m(k)\Psi_n(k) K_0'(ka) I_0'(ka) dk$$

The energy functional involving the field constraints equation is defined as $$F = W - \lambda^T(b^T J - B^0) = \frac{1}{2} J^T W J - \lambda^T(b^T J - B^0)$$

To seek the minimum condition of the energy functional, the F functional is minimized with respect to the current column vector J, i.e., $$\frac{\partial F}{\partial J} = J^T W \; \lambda^T b^T = 0$$

then we arrive the following minimum condition equation involving the current density, WJ=bλJ=W¹bλ

Using the field constraint equation as another independent equation:

$b^T J = B^0$

First, the Lagrange multipliers can be solved in the following linear equation, which combines both minimum condition and field constraint equations above.

$b^T W^1 b\lambda = B^0$

Using these values for these Lagrange multipliers, the surface current density for the coil can be uniquely determined as J=W¹bλ and then the current density is $$J_\phi(z) = \sum_{n=1}^N J_n \sin(k_n z)$$

The total current for one half of the coil is given by $$I_{total} = \int_0^{L/2} J_\phi(z) dz = \sum_{n=1}^N J_n \frac{1-(-1)^n}{k_n}$$

If the number of turns is set to $N_{turn}$, the individual current can be determined as $$I = \frac{I_{total}}{N_{turn}}$$

The inductance of the coil with N turns on one half of the coil is, $$L_{inductance} = \frac{2W}{I^2}$$

To determine the position for each current loop, the following integration of the current density is computed from the center of the coil, $$I_{total}(z) = \int_0^z J_\phi(z')dz' = \sum_{n=1}^N J_n \frac{1\cos(k_n z)}{k_n}$$

This integration allow the finding of all the spatial intervals for a total of N different discrete current wire loops. The exact location of each wire along the z-axis can be determined as the center of mass over the corresponding interval.

$$z = \frac{\int_z^{z+} z J_\phi(z')dz'}{\int_z^{z+} J_\phi(z')dz'}$$

In conclusion, a means for optimization of the intracoil distribution of coils within each microcoil in an opposed pair of microcoils may be based on these or alternative mathematic modeling of the effects of current, coil properties, and individual coil or winding positioning and design. This particular scheme has been developed for a cylindrical shaped RF coil, the technique allowing a straight forward procedure in performing a design optimization for the current loop positions of an intravascular, intracavitary, intraparenchymal, or intraluminary MR imaging coil.

Figure 4A:
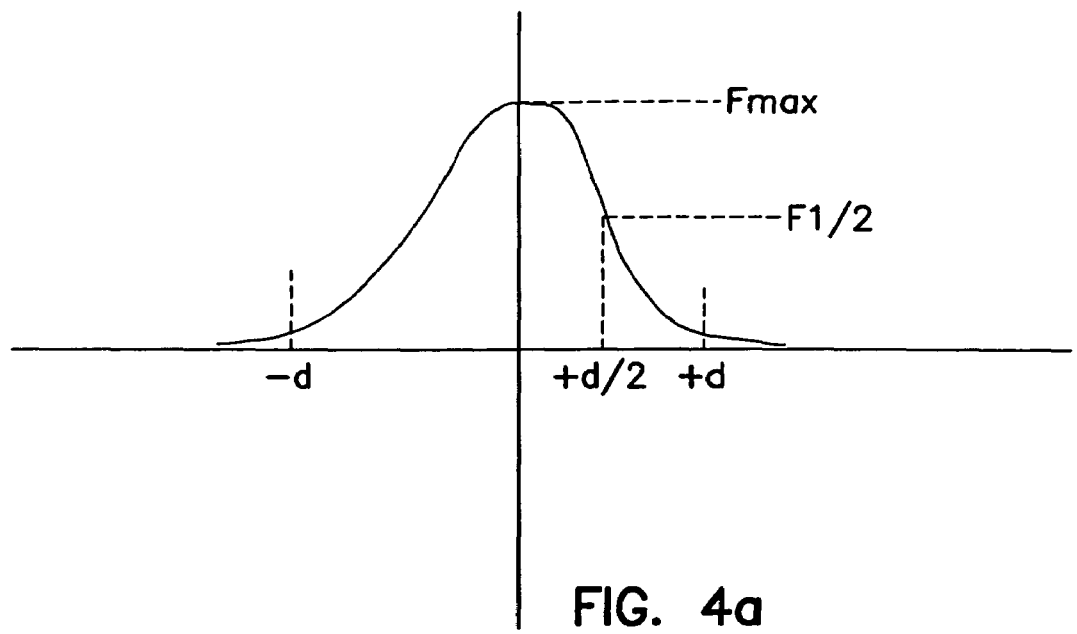
FIGS. 4a and 4b show the positioning of magnetic tips at the distal end of a delivery device in two of many embodiments of the present invention.
Figure 4B:
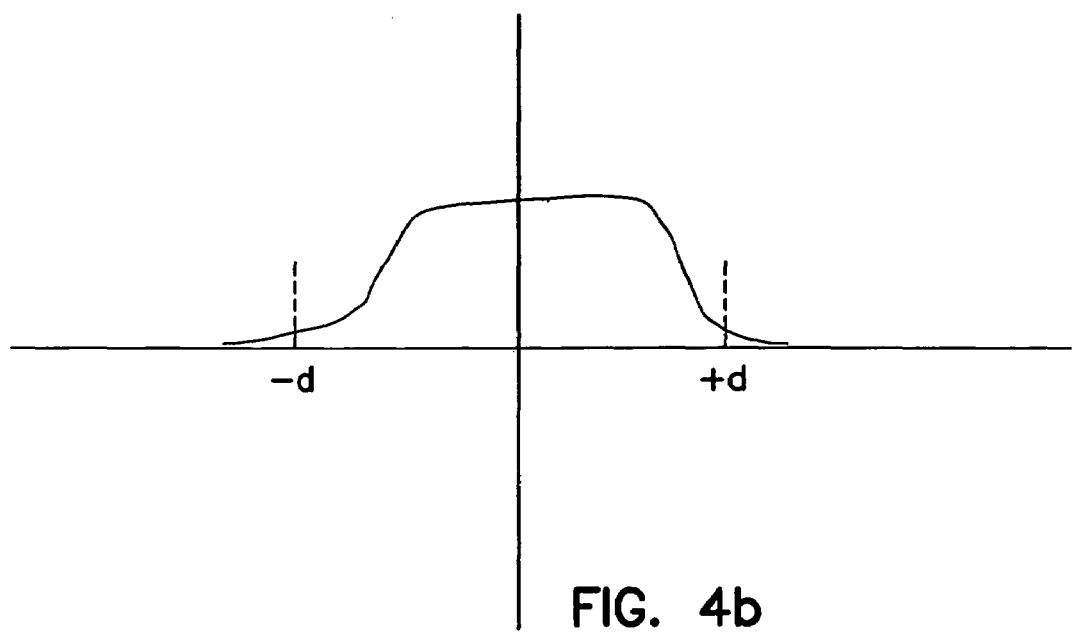
Figure 4C:
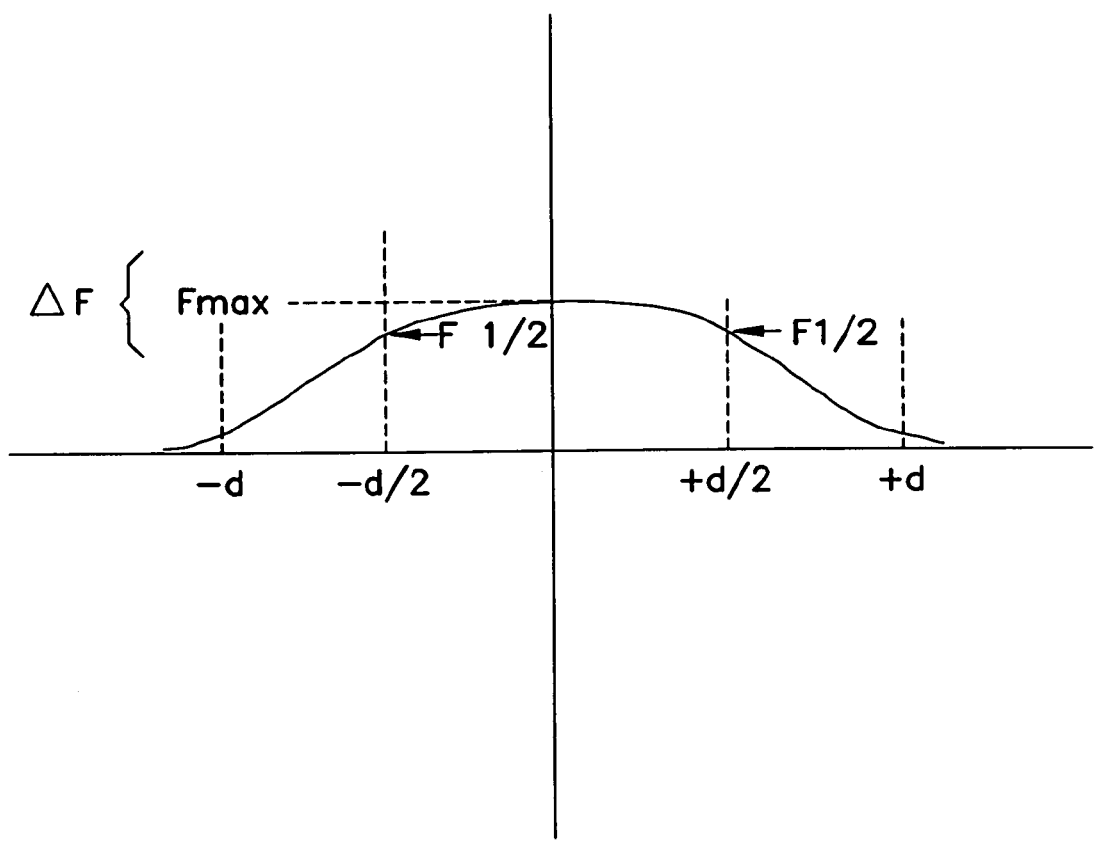
Figure 5:
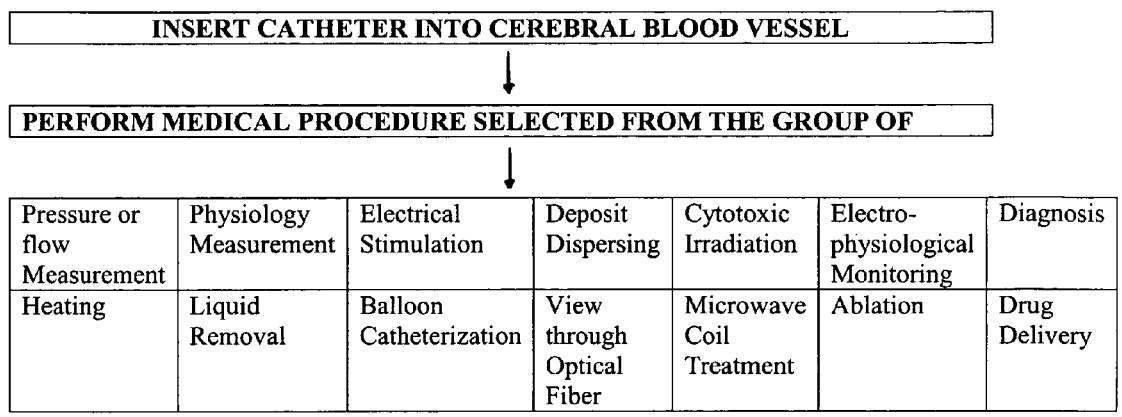
FIG. 5 is a flow sheet representing aspects of the invention.

Reference to FIG. 4 (a, b and c) will help to explain the way in which modification of intracoil design can benefit performance of the catheters of the present invention. FIG. 4a shows the Field Strength (y axis) as a function of distance away from a central point in the gap (e.g., midway between nearest ends of opposed microcoils separated by a distance of 2 d, as represented by space 19 in FIG. 1). FIG. 4a shows the Field Strength relationship in a cylindrical device having an opposed pair of microcoils with equal size of the individual windings and equal spacing between each of the windings. As can be noted fro FIG. 4a, the maximum field strength Fmax is a relatively sharp peak, and the filed strength diminishes as the distance from the center of the gap (x=0) changes. At a point halfway between the middle of the gap (with a dimension of d from ends of the opposed microcoils closest to each other) and the ends of the opposed microcoils, the field strength will drop off significantly, typically between 25 and 50% of Fmax. This rapid and significant change in the field strength can reduce the capability of the device in providing the type and quality of image in certain procedures. FIG. 4b shows an idealized version of a field strength distribution which can be provided with design considerations of the location, shape, thickness and distribution of the microcoils according to the modeling considerations discussed above. The effects of each individual winding contribution can be calculated mathematically as shown above, and then the individual contributions added together to determine the effective field strength. Some interactive effects may be considered in the mathematic summation of individual winding effects, to match the more realistic field effects from the combination of coils. A more attainable field strength distribution is shown in FIG. 4c, where a less idealized, but significantly improved field strength distribution is shown. FIG. 4c shows the relationship of field strength and position along the cylindrical device where the device has an opposed pair of microcoils with a spacing of 2 d between the near ends of the opposed pairs of coils (as shown as 19 in FIG. 1) which has the sections of windings of the coils (in FIG. 1, e.g., 13, 15 and 17) differentially spaced (e.g., different spacing between windings 13 and 15 as compared to the spacing between 15 and 17 on the same microcoil). The field strength is more uniform near the center of the gap (where x=0) as compared to the opposed microcoil structure whose field strength is shown in FIG. 4a. The field strength does diminish as the distance from the center of the gap increases, but the diminution rate is less than that for the uniform coil windings of FIG. 4a, although less than that for the idealized results of 4b. The field strength can be expected to drop less than 20% between the center of the gap and a position d/2 which is one half the distance from the center of the gap to the near end of a microcoil. It is preferred that the field strength diminish less than 17%, more preferably less than 15%, still more preferably less than 12%, and most preferably less than 10 or less than 8% between the Fmax and the field strength at the d/2 point, midway between the center of the gap and a near end of the microcoil.

A device according to the present invention may also be described as a medical device for use within an organism, said medical device comprising an element having at least one pair of opposed RF receiver microcoils having a space between each microcoil of said pair of microcoils, said RF receiver microcoils each comprising at least three individual coils, said at least three individual coils of said microcoils having spacing between adjacent microcoils so that spacing between at least two pairs of individual coils within said microcoils differ by at least 10%. The spacing between pairs of the individual coils (or windings) as measured along a line within the plane within which the microcoils reside and parallel to the axis of the cylinder (or other shape) on which the surface lies may be at least 12%, at least 15% or at least 20% or more, as compared to other spacings between adjacent windings to effect improved results in the field strength distribution within the gap.

Another design configuration which is allowable in the structures useful in the practice of the present invention is to have two layers of microcoils within the region defining one half of a pair of microcoils. That is, a first set of microcoils angled towards the gap may be located within one layer of the MR observable device, and a second set of microcoils (e.g., a set of windings) also may be angled towards the gap, but be located within an insulated layer overlaying or underlying the first set of microcoils. The spacing between coils in the sets of similarly angled microcoils may be of the same or different thickness, the same or different spacing between coils, and/or the same or different angles (although they both must be angled towards or both be angled away from the gap). The device may have at least one set of microcoils wherein a half of said at least one pair of microcoils comprises at least four windings having at least three spaces between adjacent windings of dimensions space 1, space 2 and space 3, wherein at least one of said at least three spaces does not equal the dimensions of at least one other of said spaces.

Many available technologies and structural considerations known in the art may be included within the practice of the present invention, even if some of these considerations are used within the novel structural designs of the present invention. For example, the composition of the lumen 4, support material 34, and catheter casing 40 may be selected from amongst known biocompatible materials which have been developed for medical uses. The microcoils and circuitry forming a part of the catheter system may be provided by known techniques, even if those techniques have not heretofore been used within the medical device field. For example, the microcoils could be provided by wrapping filament of conductive material (especially copper, copper coated materials, and other RF antenna materials known in the art) or by forming the filaments on or over the lumen. Such forming processes would include deposition processes, growth deposition processes, deposition and etching processes, microlithography, masked deposition, and the like. The deposition processes may include such varied technologies such as plating, electroless plating, sputtering, seeded growth, (e.g., U.S. Pat. Nos. 4,775,556 and 4,710,403), high energy deposition or etching processes (e.g., U.S. Pat. Nos. 5,389,195 and 5,332,625), chemical deposition and etching processes, etc. The techniques for providing circuitry and wiring shown in U.S. Pat. Nos. 5,106,455; 6,167,625; and 5,269,882 are examples of other technologies generally useful in the deposition of circuitry on filamentary articles and surfaces.

Figure 2:
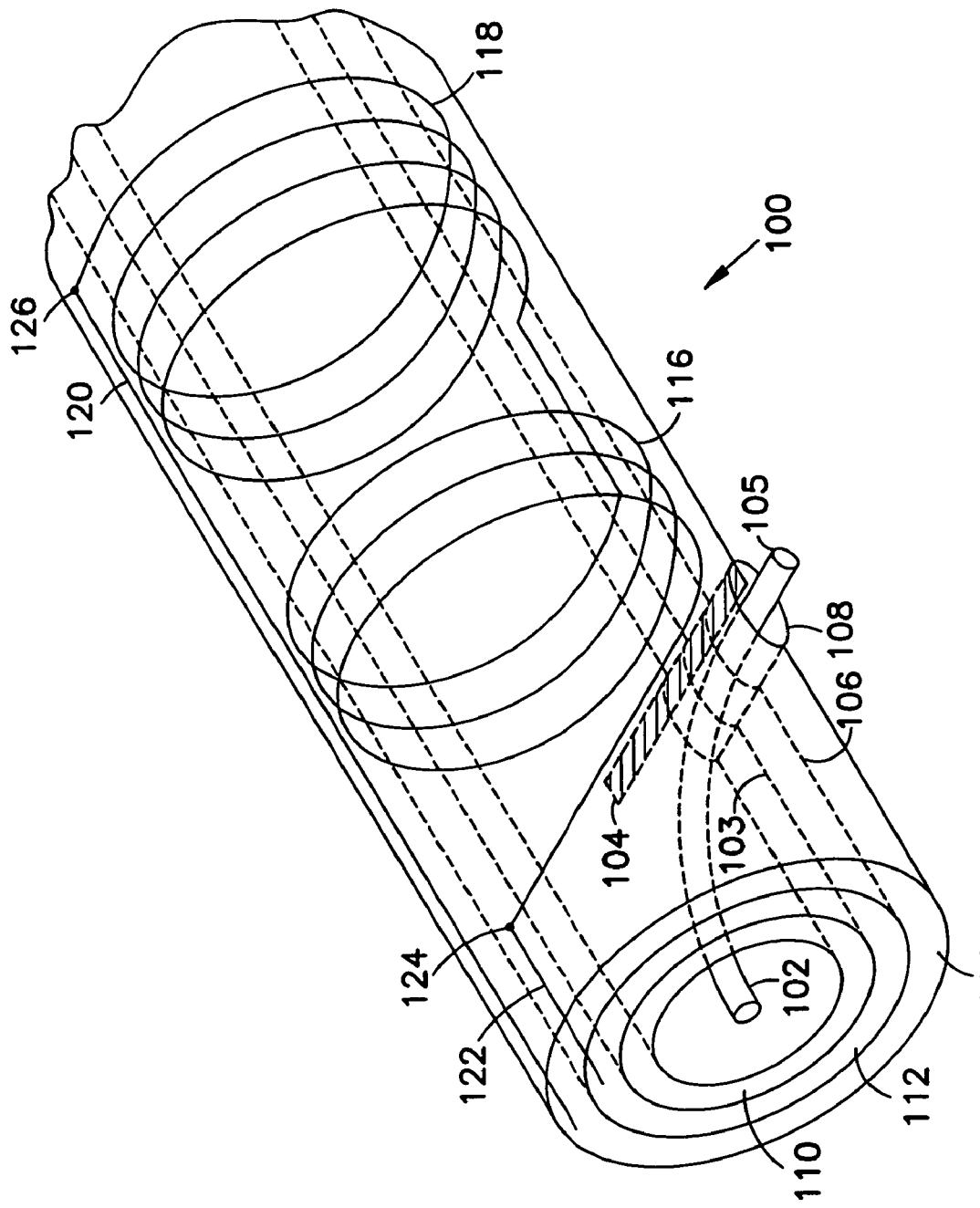
FIG. 2 is a view of another embodiment of the device according to the present invention, and it shows a flow diagram for practice of the process of the present invention wherein the drug delivery device is positioned by nonlinear stereotaxis under MR guidance and then delivery of a drug is monitored by visualization of delivery.

FIG. 2 shows a sectional view of a mid-range portion of a catheter 100 according to one configuration which may be used in the present invention. A microcatheter 102 is shown to have been deflected against an internal guiding element or deflector 106 so that and end 105 of the microcatheter 102 extends out of the catheter 100 through a hole 108 in the walls of the catheter 100. The microcatheter 102 has been deflected by the deflector 104 and rests against the deflector 104 beginning at a contact point 103. The hole 108 passes through what is shown in this FIG. 2 as three layers 110, 112 and 114 of material making up the substantive walls of the catheter 100. The deflector 104 helps to guide the microcatheter 100 into and through the hole 108. There would be a hole and deflector for each microcatheter which exits from the catheter (and these microcatheters may be provided with their own intrinsic microcoils) and these microcatheters (not shown) exits from the catheter 100, unless two or more microcatheters were to exit from a single hole, which is not a preferred construction simply for the reason that this would cause a major portion of the effects of the microcatheter (e.g., drug delivery) to occur in a limited area with respect to the surface of the catheter 100. The device may have at least three deflectors for directing each of at least three microcatheters through at least three distinct ports.

Also shown in FIG. 2 are a pair of microcoils 116 and 118. These microcoils 116 and 118 have been shown to be embedded within layer 112 of the catheter 100. It is highly desirable for optimal performance of the imaging and location function of the catheter 100 that signal produced by the microcoils 116 and 118 be as precise and clear as possible. The presence of other circuitry and wires within the catheter can interfere with this type of performance, and so special considerations should be taken to avoid any interference problems with the electrical and electronic functions of the various parts of the catheter and its subcomponents. For example, the wires 120 and 122 which are connected to ends 124 and 126 of the microcoils 116 and 118, respectively, must not contact the microcoils 116 and 118 except where they are intended to be electrically connected thereto (e.g., at ends 124 and 126). This can be accomplishes in a number of different ways according to the practice of the present invention. There is less structural potential for problems of this type with the proximal microcoil 116, because its end 124 may be connected to a wire 122 and not pass over the coil circuitry. The wire 122 may therefore be located within the same layer 112 as the coil 116. With the distal microcoil 118, the wire 120 must pass back over both coils 116 and 118 and could contact or otherwise readily interfere with any signal coming from the microcoils 16 and 118. To prevent this, the microcoils 116 and 118 are shown within a single layer 112, but the wire 120 from the distal microcoil 118 is shown within layer 124 to reduce or eliminate any electrical or electronic interference or interaction with the coils 16 and 118 or other circuitry (not shown) in the catheter 100. The separation of these respective elements into separate layers can be accomplished according to numerous techniques available within the general manufacturing art once the need has been recognized for the appropriate location of the elements. For example, once microcoils have been laid down (by wrapping, deposition or etching, for example), a polymer or other insulating material may enclose the microcoils in a distinct layer (e.g., layer 112). Once this protective or enclosing layer has been established (with appropriate electrical connection points maintained for other electrical or electronic connections), the other wiring or circuitry may be then constructed on that covering enclosing layer (e.g., 112). This additional wiring or circuitry may be constructed by processes similar to those processes used to make the coils or other processes known to those skilled in the art, including wrapping, gross application of premade circuitry, deposition of circuit or wire elements, etching of circuits or wire elements, and other construction or microconstruction techniques known in the art. A main objective of this optional structure within the practice of certain constructions of the present invention is to provide circuitry and/or wiring within distinct layers (even if of the same polymer binder composition) of the catheter. The location of the wiring or additional circuitry is done with an intent to minimize crosstalk, interference, interaction or other related effects which could be detrimental to the performance of the microcoils and circuitry. Specific interactive wave effects or field effects could be considered in the design of the location of the respective elements in performing these considerations.

A composite catheter for MR image monitored drug delivery according to certain aspects of the present invention may concern a composite device (needle or catheter) or other with a built in micro-imaging coil for MR imaging (spectroscopy) monitoring or other physiological monitoring during a therapeutic procedure. The micro coil can be interfaced to a conventional MR scanner to image the pathological change of the region at immediate proximity to the coil as well as the therapeutic site with a very high signal to noise ratio without interrupting the drug delivering process. These types of devices will become highly desirable in the near future for many neurological transparenchymal or endovascularly therapeutic applications.

One of the composite devices is shown schematically in FIG. 1. As illustrated in FIG. 1, the catheter has a number of micro size tubes 24, 26, 28 and 30 in the lumen 4 for performing various functions such as physiologic measurements, drug delivery, material withdrawal, sampling, temperature moderation or alteration, electrical stimulation, and the like. At the tip of the catheter, there exists a micro coil 10 along with a micro sized pre-amplification unit 22 for MR imaging and spectroscopy.

In general, such a composite device (or catheter) includes at least a micro-imaging coil which can be broken down into four modular parts as shown in FIG. 2:

1). Optimized imaging coil or electrode
2). Pre-amplification and decoupling integrated circuit
3). Signal transmission and shielding
4). Remote matching circuit.

Although these four parts are not necessarily separated from each other for a specific composite device design, the separation of modules are only meant for the ease of the following description.

In most cases, some of these modules are often integrated into one composite unit. The micro coil for MR imaging can be one of the following: a single loop, twisted wires, two opposed solenoids. All of these coil designs are extremely sensitive to the immediate region close to them. The detailed spatial sensitivity profile of a specific coil depends on its conductor pattern.

For the opposed solenoids, the primary magnetic field flux for reception is squeezed out at the gap between the two coils (in a direction generally perpendicular to the windings and/or the axis of the cylindrical device around which the coils are wound or formed), the number of winding required is about at least about three, more preferably between three and twenty, still more preferably between 4 and 16 for each coil, and most preferably with 5 to 12 coils with a diameter of each coil on the order of 0.1 to 2.4 mm possible, more preferably diameters of 0.3 to 2.0 mm are used, and most preferably 0.5–2.0 mm diameters are used. By depositing the coils onto the surface, wider widths of the coils may be used with less volume being taken up by the coils, with thin layers of materials being deposited as the coils (e.g., with thicknesses of a few microns being possible, up to thicknesses equal to the width of the coils) depending on the size of the catheter. Although the coil is wound or deposited on a cylindrical surface of a small diameter, there exist some degrees of freedom for optimization. For the solenoid coil design, one of the degree of freedom is the spacing between the windings. To a certain extent, the design of the micro size coil can be numerically optimized for producing a desirable reception field pattern (uniformity) in space under the geometric shape constraint imposed by a given clinical device. Using a target field method, the conductor pattern can be numerically optimized to closely match any targeted reception field pattern. The coils within the microcoils may be formed or wound with spacing of from 2.0 coil diameters between centers of adjacent coils (so that the spacing between outer sides of adjacent coils is equal to the diameters of the individual coils) up to 10 coil diameters between centers of adjacent coils (so that the spacing between outer sides of adjacent coils is equal to nine diameters of the individual coils). Preferably the spacing is between 2.5 and 8 diameters, more preferably between 3 and 6 diameters.

Furthermore, the material for the wire of coil can be any non-magnetic metal or metal alloys with a similar magnetic susceptibility as that of the human tissue. For example, the preferred materials can be simply copper, silver, Al and copper-Al composite. Both copper and silver are diamagnetic, and Al is paramagnetic. For minimizing the field disturbance, the coil conductor wire can be made to have multiple concentric layers of different metallic materials (Cu $\chi=-9.7 \times 10^{-6}$ and Al $\chi=+20.7 \times 10^{-6}$). The exact layer thickness or radius for different metal components can be numerically optimized for different size of the wires. For a zero susceptibility cylindrical shaped wire, the ratio of the radii is given by $$\frac{r_{out}}{r_{in}} = \frac{[\chi \text{out} - \chi \text{in}]^{1/2}}{[\chi \text{out}]^{1/2}}$$

Figure 3A:
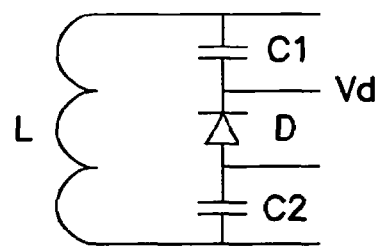
FIGS. 3a and 3b show schematic representations of circuitry for the catheter of the present invention.
Figure 3B:
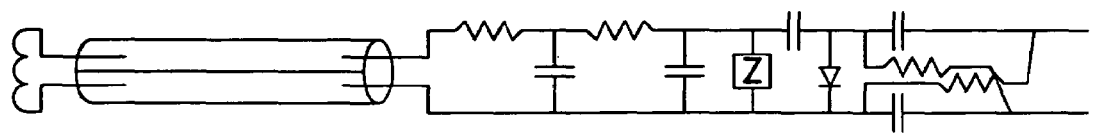

To minimize the mutual coupling between the microcoil and the volume coil used for image excitation, a decoupling circuit is preferably incorporated on the micro coil. During the excitation, such decoupling circuit element makes the micro coil invisible to the volume coil by detuning the resonant frequency of the imaging coil away from the transmitting RF frequency. One of the designs accomplishing the coil decoupling requirement is shown in FIG. 3. Where the unit includes a PIN diode denoted by D in series with the two capacitors (C1 and C2), the image coil is shown symbolically and denoted by L. The PIN diode D can be actively switched on and off by an external control voltage Vd across the diode. When the diode D is switched on, the coil L and two capacitors C1 C2 form a resonant circuit tuned to the frequency. This is an improved version of he circuitry including a pre-amplification unit. The unit also may include a PIN diode denoted in series with only one capacitor, the diode can be actively switched on and off by an external control voltage. An FET (denoting a field effect transistor) may be provided for signal amplification at RF frequency. To protect the FET component or any other type of pre-amplification module during the RF excitation, a crossed diode can be placed in front of the FET, bypassing excess induced current during RF transmission.

The entire coil can be a composite. In another words, the entire imaging coil can be made of multiple coil elements connected in series or in a phased array fashion for simultaneously imaging at multiple locations along a catheter. All of these multiple coils can be similar or different in their geometrical shape. The imaging coil can also be non-local. That is, the coil can be spatially distributed along a significant length of a catheter (especially by consideration of modeling as shown above). For this purpose, there are many choices for the active coil components: twisted wire, two parallel wire, coaxial cable, combinations of these, etc.

In addition to the variety available in the selection of the imaging coil component, various other components, such as micro electrodes can be incorporated in the device for the cell or membrane potential measurement, pressure/flow monitoring or other physiological monitoring.

For optimal signal to noise ratio (S/N) or minimal resulting noise figure, the MR signal detected would preferably have an immediate amplification (e.g., preamplification) in a location as close as possible to the coil element. The practical catheter geometry does not provide enough room for using any conventional amplification components. For the purpose of minimizing the size of the electronic components which will be used for various signal preconditioning such as pre-amplification, we have introduced an integrated circuit module in close proximity to the imaging module. The integrated circuit module includes a pre-amplification device (or unit at RF frequency) and other auxiliary devices fabricated on a silicon chip, which is preferably less than 4 mm² in size. The same integrated circuit module is preferred to be packaged in a small non-magnetic casing compatible in shape with a given instrument design.

One of the most simple units may contain only a single FET element. With the help of the integrated circuit technology, more elements can be incorporated into one single silicon module for building more complex circuitry to achieve a better performance.

The preferred transmission module is a portion of the flexible cable along the catheter for transmitting the RF signal detected for MR imaging from the coil to a remote terminal for further signal amplification and other required processing. In preferred design contemplations, all of the components of the cable are integrated to the catheter. One of the desired requirements for the cable is that it will introduce a minimal noise contamination as well as a low signal attenuation to the minute MR signal. The other desired requirement for the cable is that it will introduce a minimal hindrance to the flexibility and the stiffness of a catheter. For achieving these requirements, there are a number of the possible alternatives for the device as follows:

1) A tri-coaxial cable (a cable with a center line conductor surrounded by two concentric layers of shielding material). One variation of the cable is that the center conductor is wound in a helical fashion along the center axis of the cable.

2) A shielded twisted wire cable (a cable with two twisted wires at the center surrounded by a concentric layer of shielding material). One variation of the cable is that the two wires are wound in a spiral or helical fashion along the center axis of the cable.

3) A shielded parallel bi-polar cable (a cable with two parallel bi-polar wires placed symmetrically with respect to the center axis surrounded by a concentric layer of shielding material). One variation of the cable is that the two wires parallelly are wound in a spiral or helical fashion along the center axis of the cable.

The shielding layer can be a layer of braided thin conductive wires as well as a layer of metallic film, or any other shielding material) which may be grounded if desired) as understood in the art which may be provided in a dimension compatible with the practice of the present invention.

The remote matching unit represents a device placed at the remote end of the device. This remote unit can be used as an extra tuning device for the imaging coil at the tip as well as a detuning (or decoupling) device. The remote match unit takes the effective impedance transformation of the transmission unit into consideration for the coil impedance matching and frequency tuning. In this design, both the transmission wire and the remote unit are used for accomplishing the tuning and detuning. In order to take advantage of the property of the transmission wire, the wire with a quarter wave or half wave length of the radio frequency if interest is used. Otherwise a transmission wire with a phase shift network which shows the same effective quarter wave or half wave length behavior can be used. The coil tuning can be accomplished with a capacitor or inductor. In addition, the size of the unit is not constrained geometrically. Since the device size for this module is not an issue, more conventional electronic components can be used. Depending on a specific design, the remote unit can be very important or of no importance.

Yet another useful design is a concept of putting all the elements at the remote unit (or distal end). The schematic circuit diagram shown above in FIG. 3 includes an imaging coil (micro or macro), transmission line, phase shift network, tuning and decoupling circuit and balloon. The Z denotes a tuning element (L or C) as a part of decoupling circuit. The combined transmission line and phase shift network exhibits a quarter or half wavelength property.

Finally, the catheter tip has a stabilization mechanism incorporated. The preferred stabilization unit can be mechanically driven, or made of memory metal control with external applied voltage signal.

A source of drug delivery can be effected by devising a multi-lumen catheter with multiple drug release sources that effectively disperse therapeutic drug agents over a brain region containing receptors for the drug, or over an anatomically extensive area of brain pathology. A preferred type of structure is described in U.S. patent application Ser. No. 08/916,596, filed on Aug. 22, 1997, but other devices which are described in the background of the art in that application could also be used in the practice of the present invention.

It should be noted that the potential exists for interactive interference between the two systems, i.e., magnetic resonance imaging and magnetic stereotaxis. This is because both modalities rely on the creation of large external magnetic fields to function as designed. The magnetic field and field gradients of the magnetic stereotaxis system are used to steer an implant within the body, and especially within the brain, while the magnetic fields of the magnetic resonance imager are used to create images of the planes of tissue within the patient's body. The magnetic fields of either one of these systems/devices can perturb the size and shape (and, therefore, the function) of the fields of the other device. It is unlikely that a clinical configuration of these systems/devices would be purposely arranged so as to cause direct interference via interaction of the fields. However, a far more likely danger is that the magnetic tip of the implanted catheter or other MSS-guided device will experience bulk-body forces and torques if the patient is placed in the MR and is subjected to the resulting magnetic field produced during the course of its functioning. Such a field could very easily cause the magnetically-tipped implant to move away from the location into which it was navigated by the clinician operating the magnetic sterotaxis system. This might produce a dangerous situation for the patient and, hence, care must be taken to insure that the magnetic tip is either removed from the catheter in the patient prior to MR imaging, or that it is otherwise deactivated or made impervious to the effects of non-MSS fields to which it might be subjected. Moreover, the presence of a relatively large magnetic dipole in the patient's body, as might arise from the presence of the magnetic tip of the implanted catheter, would create artifacts in the MR images.

One of the significant difficulties with delivery of materials such as drugs, hormones, or neurotransmitters to living tissue is assuring that the materials are delivered to the target receptor location in the intended amount, and to reduce collateral damage by a) physical impact and/or spurious tissue penetration by delivery devices and b) by cell damage from the potent effects of the drugs themselves. Many materials which are delivered to a patient, even though beneficial in the treatment of a specific condition, may be moderately or even strongly noxious or damaging to healthy tissue. It is therefore one object of conventional materials application treatment to maximize dosage to a desired location and to minimize dosage to locations which do not require the delivery of the material. Additionally, newer medical treatments may include procedures which remove unwanted deposits of materials with an expectation that the removal will be assisted by physical removal (by a withdrawal system) or natural bodily function removal (e.g., dissolution with subsequent transport through the circulatory system). Newer treatments also may attempt to stimulate the body to produce natural chemicals (of which a patient may be deficient) at an increased rate (e.g., electrical stimulation to increase the production of dopamine). Because these procedures are usually highly invasive, it would be extremely desirable to have a real time indication of immediate, transient and persistent effectiveness of the procedure. Where undesired deposits or collections of materials are being dispersed, it would be desirable to visualize the actual movement of materials to assist in collecting them (e.g., through catheters) or tracking them to assure that they are not again depositing or collecting (as in intravenous or cerebrospinal fluid blockage), or moving in segments which are too large and could cause blockage in other parts of the body as they are carried about.

Unfortunately, with in vivo delivery of materials (particularly extremely small doses in small volumes delivered by small instrumentation into tissue regions protected by the blood-brain barrier, or the brain-cerebrospinal fluid barrier, or into visually inaccessible areas), it has not been possible to observe real time distribution of the material delivery, or the dispersion or distribution of the material at the injection or infusion site within the tissue. Where even small variations or miscalculations about the location of the target sight and the delivery device can significantly affect the delivery of material and the effectiveness of the delivered material, real time observation of the material delivery is even more critical than in topical or gross (e.g., massive systemic injection) delivery events. There has been no truly effective observation system for such delivery, including delivery made by or in conjunction with magnetic stereotaxis guidance of the drug delivery system prior to the present invention.

The invention comprises a device and method for targeted intracranial drug delivery using nonlinear magnetic stereotaxis combined with real-time magnetic resonance (MR) imaging or X-ray visualization guidance and, where appropriate, additional use of conventional methods of catheter manipulation. In one preferred embodiment, the MR-visible catheter drug delivery device is guided into the distal cerebrovasculature using a combination of flow-directed, manual manipulation, and magnetic stereotaxis steering without reducing cerebral perfusion in the affected vascular territory. Some general features of magnetic stereotaxis or magnetic surgical procedures are described in the text that follows. Specific procedures will depend on the nature of the patient's malady, the location and accessibility of the lesion or target location, and the mode of use selected by the clinical operator of the magnetic stereotaxis or magnetic surgery system. In a nonlinear magnetic stereotaxis procedure, the following procedures, with desired clinical variations, provide an example of practice of the present invention. The patient may be first fitted with fiducial markers that are fixed to the skull and which are visible in both MR and x-ray images. After these markers are placed in an appropriate array on the skull, the patient is given a pre-operative MR brain scan, the results of which constitute an atlas of images that define the location of critical brain structures and any potential target locations (e.g., a specific part of a tumor) relative to the fixed fiducial markers. The atlas of images is then stored in the host computer system used by the clinician to control the magnetic stereotaxis system. Near real time, real time, or on-the-fly MR images may also be obtained and might be used to control the magnetic stereotaxis system (although this would interrupt the magnetic stereotaxis procedure to some and perhaps a large degree), and in fact, real time images provide a potentially more accurate guide path. Following any additional pre-operative procedures that might be indicated for the patient's condition (eg., sedation, full or partial anesthesia, etc.), the patient who will undergo an intraparenchymal magnetic surgery has a burr hole opened in their skull to allow the clinician an access port to insert the implant that will be magnetically guided to the intracranial target. Following placement of the implant on the pial surface of the brain within and at the bottom of the burr hole, the patient then rests their head within the configuration of coils that are used to apply magnetic forces and torques to the implant, and the clinician operates the bi-planar fluoroscopy system and other controls of the magnetic stereotaxis system. The resulting images provide 3-dimensional information about the location of the implant relative to the skull markers, and these data are superimposed and registered onto the pre-operative MR brain scan (near real time, real time or a more recent scan) so that the clinician can determine the initial position of the implant in relation to critical brain structures and/or target locations within the brain. The clinician then enters commands into the magnetic stereotaxis system's user interface that instruct the system how far to move the implant and in what specific direction. This can be done in one instance by using cursor-cross hairs, screen contact pencils, virtual drawing systems, or other graphic or viewable drafting systems on a computer screen to indicate the present location of the implant's tip and to select the next location to which it is to be moved. The clinician then instructs the system to execute this movement command and the system uses its control algorithm to produce magnetic fields that steer the magnetic tip of the implant appropriately while the body of the implant is pushed forward, as might be done by a motor-actuated guide-wire that traverses the interior of the implant/catheters/lumen, and abuts against the rear side of the tip of the implant. Biplanar fluoroscopic images are obtained during the movement sequence to localize the new position of the tip of the implant. In some variations of this procedure and with reference to prior art cited above, a multiple lumen catheter is used as the implant, and the magnetic tip of the catheter (fixed to one of the interior sub-catheters) can then be withdrawn from the implant once it is properly in place, and some other mechanism or therapy deliver device can be inserted through the outermost lumen of the catheter in place of it to perform the indicated diagnostic or therapeutic task. The implant can then either be withdrawn or left in place for any subsequent treatments that might be needed.

If the magnetic stereotaxis system is to be used as a method of delivering therapies into the cerebrovasculature, then in a manner similar to the way that interventional neuroradiological procedures are now carried out, the implant/catheter would be introduced into the body perhaps through the femoral artery and guided into the brain. The process for intra-endovascular versus intra-parenchymal manipulations is rather similar, in that a pre-operatively obtained atlas of appropriate images is used as a "road map" against which the navigation of the implant is carried out. A high resolution digital subtraction angiography atlas might be used in this case, to insure that the clinician is able to identify the vascular structures through which the implant must be moved. If the implant must be guided through vessels in which its path of movement is parallel to the flow of the blood, then the implant's movement can be partially flow-guided. Whether this is so or not, the tip of the implant is steered in the proper direction at vascular bifurcations by use of the magnetic fields to re-orient the tip as needed. The movement of the tip can be actuated by a pusher-wire or guide-wire inserted into the lumen of the implant/catheter and either driven by motor or advanced by hand, as appropriate to the implant's location, direction of movement, and targeted point of delivery. Ongoing biplanar fluoroscopy and post movement biplanar fluoroscopy are carried out for purposes of monitoring the implant's location, in ways analogous to the case of intraparenchymal magnetic manipulation described above.

Some additional general features of a magnetic stereotaxis or magnetic surgery procedure are the following. In the case of the use of a multi-coil superconducting "helmet" arrangement of the magnetic manipulation coils, the patient lies on a bed or gurney located in contact proximity with the front of the helmet, such that the patient's head can then comfortably rest inside the interior of the helmet's structure. The patient's head is immobilized on a headrest within the helmet's structure so that it does not inadvertently move during the procedure, thus introducing error and or time-delays into the imaging and image registration processes. Intraparenchymal magnetic movements would all take place in small increments and at very low rates of displacement, typically 1 mm/s or less. The intra-operative biplanar fluoroscopy is generally carried out so as to minimize the overall radiological dose received by the patient, consistent with the need for clarity in the images when that is called for. In the case of intravascular magnetic manipulation, the rate of displacement of the implant's tip through the vessel it is traversing will depend on the inside diameter of that vessel, the complexity and tortuosity of the vessel's structure and path, and the degree and direction of the blood flow in the vessel. The decision as to the selection of the rate of displacement is made by the clinician administering the treatment, using these and other factors to decide. In either case, the therapeutic agent to be delivered into the targeted area is pumped or otherwise transported through the lumen of the implant's catheter and allowed to exit from the tip of the implant or through selected regions of the side of the catheter (if it is made of a semi-permeable material). The therapeutic agent can thus be infusively pumped into the interstitial space of the brain (in the case of intra-parenchymal infusion), perfused through endothelial walls of the arterial capillaries and into the brain, or retroperfused through the venous vasculature and into the brain. To further minimize the adverse effects of improperly located retroperfusion or delivery devices, the magnetic stereotaxis guided systems of the present invention can be magnetically guided during actual drug delivery to provide the maximum quality response to diagnosis of improper or inefficient delivery. Additional interoperative Magnetic Resonance Imaging would not perturb the location of the implant that was guided by Magnetic Stereotaxis, when the magnetic tip of the catheter implant is withdrawn prior to subsequent imaging and as long as the body of the catheter or implant is not made of permanently magnetic or magnetically permeable material. In general, a magnetic resonance imaging system would interfere with magnetic stereotaxis guidance (and vice versa) during mutual operation.

In either the intraparenchymal or intravascular applications, a magnetic stereotaxis procedure may alternatively be used to tow an intracranial electrical mapping or intracranial stimulation electrode or plurality of such electrodes, or some other solid object, such as a wire, filament, contact, lead or optical fiber or optical fiber bundle, into the brain or the cerebrovasculature for diagnostic or therapeutic purposes. The magnetic manipulation process would closely resemble that described above for the movement of an implant/catheter combination. MR Imaging would then be carried out to verify that the implant or object was properly positioned, providing, of course, that the imaging process would not jeopardize the safety of the patient by risking movement or heating of the implant or object.

The intracranial drug delivery device has at least one MR-visible marker, and preferably a linearly arranged array of radio-opaque and MR-visible markers disposed along its length to provide easily identifiable reference points for trackability and localization under susceptibility and active MR imaging, and under the bi-planar X-ray fluoroscopy used during nonlinear magnetic stereotactic guidance. Moreover, the tip of the intracranial drug delivery device would be fabricated such that it can be seen on MR and x-ray images and thus localized within the brain and/or spinal cord. The location of the tip of the drug delivery device is therefore known and the source point of the injection or infusion can thus be seen relative to the location of the device.

In a characteristic embodiment of the technique, an MR-compatible osmotic pump or some other flow-driving device is connected to a variable-length concentric MR-visible microdialysis probe with a variable molecular weight cut-off membrane or some other infusion device with a magnetic tip. This assembly is directed by nonlinear magnetic stereotaxis to the cerebrovascular, periventricular, intracerebroventricular, subarachnoid, intra parenchymal or intracerebrovascular site of the lesion. With the magnetic tip then either removed, safely positioned, or otherwise inactivated, the proper location of the probe is verified by MR imaging and additional nonlinear magnetic stereotactic maneuvering, if necessary, is carried out. The pump circulates a diagnostic or therapeutic drug solution containing an MR-visible contrast agent through the walls of the dialysis fiber into the brain parenchyma or cerebral vasculature at rates between 0.01 nanoliters per hour to 10 milliliters per minute. The delivery and distribution kinetics of cerebrovascular, cerebrospinal fluid, and parenchymal injections or infusions of drug agents are monitored quantitatively and non-invasively using real-time contrast-enhanced magnetic susceptibility MR imaging combined with water proton directional diffusion MR imaging, and the response of the patient (in the case of therapy delivery) is tracked during this treatment. The distribution, pharmaco-kinetics, and (in some cases) clearance processes for the retroperfused or otherwise infused agent are tracked using the "Method and Apparatus for Use with MR Imaging" taught by Kucharczyk and Moseley (U.S. patent application Ser. No. 08/857,043, filed on May 15, 1997 and titled "Method and Apparatus for Use with MR Imaging").

The basic operation of the present invention therefore involves the initial MR imaging observation of a molecular environment of a patient or a target (e.g., a particular area or region of a patient, such as tissue, particularly such tissue as that present in organs or systems of animal bodies and especially the human body, including, but not limited to the intracranial compartment and the various anatomic regions of the brain, including the cerebral ventricles, cisterns, epidural and subdural spaces, sinuses, and blood vessels, the spinal cord, and spine, including disks, nerves and associated vascular system, the heart and the coronary vascular circulation, liver and the hepatic vascular circulation, kidney and the renal vascular circulation, spleen and the splenic vascular system, gastrointestinal system, special senses, including the visual system, auditory system, and olfactory system, the lymphatic system, the endocrine system including the pituitary gland, thyroid gland, adrenal gland, testes, and ovaries, and the peripheral parts and limbs of the body, with observation of an MR image signal intensity at a given time and/or state (e.g., prior to material introduction or at some defined stage of material diffusion into the molecular environment. In an example of the method of the invention, the drug delivery device is positioned by magnetic stereotaxis and viewed when possible and appropriate in real time by MR imaging or X-ray fluoroscopy to confirm that the device is properly positioned in a desired region (if not precise location) within a patient's body. Then the distribution of the delivered material in the tissue is determined (viewed by MR real time imaging) by releasing an amount of the material through the drug delivery device (which was already positioned in the tissue by magnetic stereotaxis and location-confirmed) while being observed with Magnetic Resonance Imaging, allowing the material to diffuse or perfuse into the tissue, and analyzing the resulting MR signal intensity. On a continual basis or at some subsequent time interval later (so as to conserve energy requirements or minimize the treatment time to or other possible effects on the patient, e.g., by a pulsed interval, preselected interval, random interval, frequent or sporadic intervals), the MR image of the molecular state within the same general area is observed. Changes in the characteristics, properties or quality of the image, such as the image signal intensity within the area are presumptively (and in most cases definitively) the result of the introduction of material into the original molecular environment and alteration of the MR response for regions of the environment where delivered material concentration has changed. By repeating observation of the MR image signal intensity within an area at least once (e.g., first taking the initial observation at a material concentration state at a time $T_1$, and at least one subsequent observation of MRI-observable changes such as in the signal intensity qualities at a time $T_2$), the change in MR image signal intensity qualities can be related to the change in material concentration (in a region or at specific site locations or even within particular cell structures) between times $T_1$ and $T_2$, whether that change is from a starting point of zero concentration or from an existing concentration level. The observations therefore relate to the actual delivery of material into the molecular environment in an observable, and to some lesser degree, quantifiable manner.

The change in the signal, e.g., the change in the amplitude of the MR signal in the visible image may be altered by:

a) a change in the apparent diffusion coefficient (ADC) of tissue water protons;
b) a change in tissue magnetic susceptibility (BO);
c) a change in T1 tissue relaxivity (T1);
d) a change in T2 tissue relativity (T2);
e) a change in tissue magnetization transfer coefficients (MTC);
f) a change in tissue chemical shift frequency;
g) a change in tissue temperature; or
h) a combination of any one or more of a)–g) alone or with other effects.

The MR signal is dephased by the random motion of diffusing water molecules, and the presence of the delivered material locally affects the degree to which the amplitude of the signal is altered by the dephasing. If the amount of active ingredient to be delivered is quite small, or the effect of that material on the alteration of the amplitude is minimal, the delivered material may be associated with a larger amount of a second material or another more MR-signal-responsive material, which are preferably selected on a basis of similarity in diffusion rates through like materials or at least have comparable (mathematically relatable) diffusion rates. In this manner, using such a taggant material, the diffusion of the delivered material may be assumed to relate to the diffusion/delivery of the taggant material. Unlike other observational techniques, these taggant materials may be readily provided as non-toxic, inexpensive taggant materials since there is such a wide variety of materials which could be so used, and their only functional requirements would be diffusion rate and non-toxicity. Many dyes commonly used in medical procedures could be used for this purpose.

The availability of an MR-visible drug delivery device, which can be guided and placed by magnetic stereotaxis and combined with a visible chemical or drug agent would make it possible to obtain near real-time information on drug delivery during interventional procedures in an intra-operative MR system, with pre- and post-imaging remote guidance of the delivery system via magnetic stereotaxis, or alternatively, real-time intra-operative guidance via an MR-based interventional technique, as well as for pre-operative and post-operative confirmation of the location of the drug delivery device. Medical and surgical applications would include vascular surgery and interventional radiology, cardiac surgery and cardiology, thoracic surgery and radiology, gastrointestinal surgery and radiology, obstetrics, gynecology, urology, orthopedics, neurosurgery and neurointerventional radiology, head and neck surgery and radiology, ENT surgery and radiology, and oncology. In addition to direct tissue injection, the method of the invention applies to drug delivery via intraluminal, intracavitary, laparoscopic, endoscopic, intravenous, and intra-arterial applications.

There is currently considerable interest in the therapeutic use of small ions as well as macromolecules in the treatment of various neurologic diseases. To be effective, such molecules must be able to reach target tissue receptors. Many molecules that are used in therapeutic drugs are large in size, for example, neuroleukin, a neuromodulator drug tested for treatment of amyotrophic lateral sclerosis is about 56 kDa, bethanechol chloride used in treatment of Alzheimer's Disease is about 196 kDa and nerve growth factor is about 13 kDa. While the importance of large molecular weight molecules in direct parenchymal drug therapy is growing, little is known about the time course and the spatial range of their actions, since dynamic visualization methods for studying the spread of macromolecular species within the brain are not typically available.

Partly because of this, several significant efforts recently have been undertaken towards the goal of developing an understanding of the diffusion of various molecular species through the interstices of the neural tissues. The work has followed two general lines of activity: (1) the development of new experimental approaches that overcome the existing limits on the laboratory study of the temporal and spatial distribution patterns produced by the diffusion or spread of an agent through the central nervous system (CNS), and (2) attempts to analytically describe this process in terms of suitable mathematically-based biophysical models of the diffusion or spread of such agents through the CNS. In addition to understanding the diffusion-based transport of metabolic or therapeutic agents in the brain, it is also important to have a clear perception of the infusion-based transport of such agents. This is because such agents would typically be delivered in aqueous solution (or at least in liquid form) by a drug-delivery catheter that inserts them, e.g., into the parenchymal tissues under conditions in which pressure gradients can and typically would subsequently exist in the brain (at least within regions of the brain in the vicinity of the infusion site). These gradients, in turn, can and typically do produce hydrodynamic driving forces on the infused solutions. Both biophysical mechanisms, infusion and diffusion, contribute to the movement of molecules through the CNS and both are important delivery processes that could be enabled and would be optimized by the subject invention, i.e., an MR visible catheter that can be placed within the brain or neurovasculature via magnetic stereotaxis. Those features of these mechanisms that are important within the context of the subject invention and which help to reveal its full utility are presented below.

Basser has developed a biophysical model for infusions through a porous medium like the brain ("Interstitial Pressure, Volume, and Flow during Infusion into Brain Tissue," Microvascular Research, Vol. 44, pps. 143–165, 1992). In particular, he uses a consolidation model to predict the dynamic response of the brain's structure to the pressure-driven infusion of a fluid within the brain. He then examines the pressure and flow distributions for infusates pumped into the brain under four different conditions. (1) infusion from a constant pressure source, (2) infusion from a constant flow source, (3) step infusion from a pressure source, and (4) step infusion from a constant flow source. Infusion from a constant pressure source is a model that is applicable to the delivery of drugs into the bulk brain tissues, and one of the results of Basser's study is the prediction that the velocity, $V_r(r)$, of the fluid infused within the brain is a function of the radial distance, r, from the infusion point, and that the specific prediction is that $V_r(r)=kP_o a/r^2 f$ where k is the hydraulic conductivity of the brain matrix material, Po is the pressure within the cavity created in the brain matrix at the tip of the infusion source (eg., the catheter tip) by the initial influx of fluid, a is the radius of the initial infusion cavity, and f is the volume fraction of the interstitial space relative to the total brain volume. The penetrability of fluids agents delivered via pressure-driven infusion is generally different from that associated strictly with diffusion of the same substances, since the driving mechanisms are different (infusion: flow along a pressure gradient; diffusion: flow along a concentration gradient). This is an important point since diffusion alone may not constitute a completely effective driving mechanism for all of the different fluid agents that must penetrate certain regions of the brain e.g., those with elevated interstitial pressure, such as solid tumors (for a discussion of elevated intersitial pressure in tumors, see Netti et al., "Time-Dependent Behavior of Interstitial Fluid Pressure in Solid Tumors: Implications for Drug Delivery," Cancer Research, Vol. 55, pps. 5451–5458, 1995). Moreover, Morrison et al. ("High-Flow Microinfusion: Tissue Penetration and Pharmacodynamics," American Journal of Physiology, Vol. 266, ps. R292–R305, 1994) have shown that volumetric infusion rates of 0.5 µl/min and above are potentially able to provide dosages of agents to much larger volumes of brain tissues than are possible with lower-flow rate methods. These points, taken in conjunction with clinical testing of the infusion concept (Lieberman et al., "Convection-Enhanced Distribution of Large Molecules in Gray Matter During Interstitial Drug Infusion, Journal of Neurosurgery, Vol. 82, pps. 1021–1029, 1995; Laske et al., "Chronic Interstitial Infusion of Protein to Primate Brain: Determination of Drug Distribution and Clearance with Single-Photon Emission Computerized Tomography Imaging, Journal of Neurosurgery, Vol. 87, pps. 586–594, 1997; Broaddus et al., "Distribution and Stability of Antisense Phosphorothioate Oligonucleotides in Rodent Brain Following Direct Intra parenchymal Controlled-Rate Infusion," Neurosurgical Focus, Vol. 3, No. 5, Article 4, 1997), suggests the utility of the method for treating a wide variety for neurological disorders, providing that a suitable means of placing the catheter within the brain and verifying its proper location therein can be employed. The present invention provides appropriate methodology for allowing this to happen.

Diffusion of drug and/or water protons in a complex medium, such as a brain cell microenvironment, is influenced by numerous factors. Materials injected into the brain or spinal cord do not move unimpeded through the aggregations of neurons, glia, capillaries, and nerve fibers. The distribution of a drug volume in the brain cell microenvironment following injection directly into brain tissue is governed by a number of factors including the physicochemical characteristics of the drug, capillary uptake, metabolism, excretion, size of the extracellular space (the volume fraction), and geometry and topology of the brain cell microenvironment (tortuosity). The degree to which each of these factors influences the distribution of a particular drug agent within the brain or spinal cord is an important determinant of the effectiveness of drug treatment of diseases of the central nervous system.

Despite the fact that the average spacing between brain cells may be no more than 20 nm, the mean free path of an ion at the typical ionic strength of the mammalian nervous system (about 0.15) is only about 0.01 nm. In ways similar to altering the local ADC of the water protons, presence and transport of a drug through a tissue will also alter the magnetic susceptibility, T1, T2, MTC, water proton diffusion anisotropy, chemical shift frequency, and temperature of the protons within each imaged voxel. This represents the distance traveled between collisions with other molecules. Almost all these collisions actually take place with water molecules since the concentration of water is 55 M. Thus ions intrinsic to the brain rarely encounter cell membranes and generally behave as though they were in a free medium. However, the diffusivity properties becomes much more complicated when the boundary has a complex geometry, or when macromolecular interactions involve exogenous solutions injected into tissues.

In complex media such as brain tissue, diffusion obeys Ficks Law, subject to two important modifications. First, the diffusion coefficient, D, is reduced by the square of the tortuosity factor to an apparent diffusion coefficient ADC*=D/(tortuosity factor)$^2$ because a diffusing material encounters membranous obstructions as it executes random movements between cells. Second, the source strength is divided by the volume fraction of the extracellular space so that a given quantity of released material becomes more concentrated than it would have been in a free medium.

In most media, tortuosity and volume fraction are essentially dimensionless factors which depend only on the geometrical constraints imposed by local structures. In brain tissue, however, a third factor, non-specific uptake, is present in the diffusion equation as a term, k', for loss of material across the cell membranes. In fact k' can be expressed as P(S)/volume fraction, where P is the membrane permeability and (S) is the volume average of the membrane surface area. Complex local boundary conditions imposed by cell membranes can thus be removed by averaging the local diffusion equations and boundary conditions over some characteristic volume of tissue a few micrometers in extent. Thus in the case where a substance is injected from a point source at a rate of q moles/s in a free medium, the source term becomes q/tortuosity in a complex medium while the diffusion coefficient is modified to be D/(volume fraction)$^2$ in the new equation, which then becomes a quantity related to the apparent diffusion coefficient, ADC.

Knowledge of the properties of the brain extracellular microenvironment is thus essential to understanding the role of diffusion in delivering metabolic or therapeutic agents to brain or spinal cord cells. Diffusion has been determined employing radioactive or fluorescent tracers, in which the concentration profiles of the tracer are monitored over time, and its diffusivity is inferred from the data. Microscopic displacements can be seen with tracers on the scale of millimeters. Spatially resolved methods, such as infrared spectroscopy or Rayleigh scattering, have been used allowing resolution in the micrometer range. Such tracer techniques have been successfully applied in biological systems, such as the brain. However, because of the inherent invasiveness of using exogenous tracers, such techniques cannot be used in vivo with humans.

Techniques have also been developed for determining the diffusion characteristics of small molecules in local regions of the brain using radiotracers, microiontophoresis, or pressure microinjection combined with ion-selective microelectrodes. The applications of these methods to intracranial drug delivery have been described in the medical literature, for example, Lux et al., Exp. Brain Res., 17, 1973, pp. 190–205, Gardner, Medwin, Neurosci. Res. Progr. Bull., 1980, 18, pp. 208–226, Nicholson et al., J. Physiol., 1981, 321, pp. 225–257, Nicholson et al., Brain Res., 1979, 169, pp. 580–584. However, these techniques have several key limitations. First, these techniques provide a measurement at only a single point in the tissue so that spatial patterns of diffusion cannot be determined. Second, ion-selective microelectrodes can only be used with a few small ions. Third, radiotracer techniques rely on postmortem counting of particles in fixed and sectioned tissues, and they provide limited spatial resolution with no dynamic information.

Several previous studies have obtained estimates of the ADC of large fluorescent molecules from digitized images of fluorescent molecules as they diffused away from blood vessels. However, the complicated geometry of the source and inability to precisely characterize the emitted flux, substantially limit the clinical utility of the information. Similarly, new optical imaging methods, in which a uniform distribution of fluorescent tracer is first established in the sample and then a region is photobleached with a strong laser, has serious limitations because the laser beam can also damage the tissue area being imaged. Studies with optical fluorescence methods suggest that molecules as large as 70 kDa can pass through the brain extracellular microenvironment. Further studies with positive pressure infusion, however, show that Blue Dextrain molecules with molecular weights of 2,000,000 can be pumped through the interstitial space of the brain. (S. S Prabhu, W. C. Broaddus, G. T. Gillies, W. G. Loudon, Z. J. Chen, and B. Smith, "Distribution of Macromolecular Dyes in Brain Using Positive Pressure Infusion: A Model for Direct Controlled Delivery of Therapeutic Agents," *Surgical Neurology*, Vol. 49 (1998).

Below some limit between 10 and 40 kDa, molecular diffusion is not restricted any more than with much smaller molecules. Similar constraints have been found for diffusion in the brain intracellular microenvironment, whereby all molecules diffuse at least three times slower than in aqueous solution, suggesting a similar tortuosity in the intracellular environment.

An integrative optical imaging technique disclosed by Tao and Nicholson, Biophysical J., 1993; 65, pp. 2277–2290 yields an apparent diffusion coefficient from digitized images, and enables precise determination of the diffusion characteristics of fluorescently labeled compounds of high molecular weight. The generalized equations disclosed by Nicholson and Tao have two nondimensional factors that incorporate the structure of the tissue into the imaging solution. The first factor, the tortuosity, accounts for the hindrance to extracellular diffusion that arises from the obstructions presented by cell membranes. The second structural factor is the volume fraction, which is defined as the ratio of the volume of the brain extracellular microenvironment to the total volume of tissue averaged over some small reference domain. The method disclosed by Nicholson and Tao ("Hindered diffusion of high molecular weight compounds in brain extracellular microenvironment measured with integrative optical imaging." Biophysical J. 1993; 65:2277–2290) does not, however, yield a direct measurement of the molecular distribution in a three-dimensional sample, and furthermore requires the use of large fluorescent markers which are not suitable for repeated injections in human patients.

An alternative approach to measuring diffusivity of therapeutic drug injections is to monitor the diffusion process itself, i.e., the random motions of an ensemble of particles. Einstein showed that the diffusion coefficient measured in nonequilibrium concentration cell experiments is the same quantity that appears in the variance of the conditional probability distribution, $P(r/r_o, t)$, the probability of finding a molecule at a position r at a time t, which was initially at a position $r_o$. For free diffusion, this conditional probability distribution obeys the same diffusion relation. Thus, MR imaging parameters which reflect the differences in relative water proton-diffusion path lengths may serve to enable imaging differentiation between tissue water protons and protons in macromolecular solutions that are injected into brain tissues.

Molecular water-proton diffusion is caused by thermally induced random Brownian motion. As the protons continually collide with their microenvironments, their average random traveled pathlength <L>, along one direction (e.g., along the magnet-bore direction) is described according to Einstein as: $<L^2>=2\,TD$ where over an observation time of T (seconds) the displacement is expressed by a "diffusion coefficient, D" in $r=2/S$ or $CM^2/S$. The diffusion process is continuous, so that the average displacement of any population of water protons increases with MR imaging time. However, the diffusion behavior of protons can be hindered by impermeable or semi-permeable barriers, such as cell membranes, and macromolecules, which may themselves contain populations of diffusing protons. For tissue water protons diffusing within a tissue matrix, the observed diffusion rate and direction will reflect the molecular and macromolecular barriers or hindrances that the diffusing protons encounter during their translational processes. One example of the application of this concept in human neurobiology is that myelinated nerve fibers in the brain and spinal cord preferentially dispose the diffusion of water protons along, rather than across, myelin tracts thereby giving rise to diffusional anisotropy MR imaging properties (Moseley et al., Mag. Res. Med., 19, 1991, pp. 321–326, Moseley et al., Topics Mag. Res. Med., 3, 1991, pp. 5068).

Although noted for its effects on high-resolution, high-field MR spectra more than 25 years ago, molecular (water proton) diffusion has just recently been shown to have an important impact in clinical MR neuroimaging applications. While T1 and T2 relaxation times reflect frequency-dependent rotational and proton exchange processes, diffusion is caused solely by molecular or proton displacements or translations. Molecular size, shape, microenvironment, and temperature all influence the diffusion rate of molecules.

Generally, larger molecules will translate (diffuse) more slowly than smaller molecules, such as water protons, and the differences in diffusion rates between different populations of molecules can be distinguished by signal intensity differences on diffusion-weighted MR images, particularly MR images which employ large diffusion gradients (b values). Thus, the measurable diffusion of smaller versus larger molecules with MR imaging can be used as an in vivo tracer to probe the structural orientation of the tissues into which the drug agent has been injected. Advances in diffusion-weighted MR imaging have been made possible by major technical improvements in MR scanner hardware and software. High-speed MR echo-planar imaging now enables subsecond diffusion-sensitive imaging of water proton behavior in brain and spinal cord.

Thus, MR-visible molecules may exist in a variety of environments in brain tissue, which modify the way in which the molecules can move. First, the space in which the molecules can move may be small (e.g., intracellular) or large (e.g., an enlarged extracellular space). Second, the amount of dissolved compounds and proteins may alter the viscosity of the substance injected into the tissue. The random movement of the molecules is characterized by its diffusion coefficient ADC as the mean square distance moved for unrestricted isotropic (i.e. same in all directions) diffusion (for example a large sample of pure water). ADC is high in pure water, and lower by about a factor of 10 in tissue. As tissue becomes destroyed by disease processes, ADC is expected to rise toward its free water value. A prerequisite for MRI-guided drug delivery into the brain parenchyma or cerebral vasculature is the availability of suitable access devices. Representative of dilatation catheters having a coating which releases a therapeutic agent is U.S. Pat. No. 5,102,402 to Dror, in which a microencapsulated compound is released upon expansion of the dilatation balloon into contact with the surrounding tissue. U.S. Pat. No. 5,171,217 to March describes the delivery of several specific compounds through direct injection of microcapsules or microparticles using multiple-lumen catheters, such as disclosed by Wolinsky in U.S. Pat. No. 4,824,436. U.S. Pat. No. 5,120,322 to Davis et al. describes the process of coating the surface layer of a stent or shunt with lathyrogenic agent to inhibit scar formation during reparative tissue formation, thereby extending exposure to the drug agent. U.S. Pat. No. 5,057,106 to Kasevich discloses the use of microwave energy for heating atherosclerotic plaque in the arterial wall in combination with dilatation angioplasty. U.S. Pat. No. 4,807,620 to Strul and U.S. Pat. No. 5,087,256 to Taylor are examples of catheter-based devices which convert electromagnetic radiofrequency (RF) energy to thermal energy. U.S. Pat. No. 5,628,730 to Shapland et al discloses a phoretic balloon catheter with hydrogel coating which can be used to deliver drugs locally to internal body tissues under x-ray visualization. U.S. Pat. No. 5,720,720 to Laske et al. Describes a catheter-based high-flow microinfusion method which has been used to infuse substances up to 1 cm from the delivery source.

The patented inventions referenced above provide useful methods for introducing, delivering, or applying a drug agent to a specific target tissue, but each invention also has inherent limitations, some of which can lead to technical and clinical difficulties. With currently used catheterization techniques, there is generally a compromise between longitudinal and torsional rigidity for advancing and negotiating progressively more tortuous and narrow vascular lumens. As a result of these limitations associated with transarterial and transvenous manual catheterization, there has been growing interest in using magnetic fields to guide catheters through the cerebral vasculature. As an example of another common catheter design problem, catheter systems which provide endovascular drug delivery either require temporary blocking of a segment of the vessel, or the use of significant transluminal pressures to induce penetration of the drug agent into the vessel wall or plaque layer. Microencapsulated coatings on catheters permit longer exposure of the tissue to the drug agent, but the physical limitations imposed by microcapsules restrict the volume and concentration of drug that can be effectively applied to any tissue area. Exposed coatings on catheters which contain drug agents usually require some type of sheath that must be removed from the catheter before the drug can be released from the coating. The sheath and any catheter components required to physically manipulate the sheath greatly increase the profile of the catheter, and may thereby limit the variety of applications for which the drug delivery system can be employed. Furthermore, the binders or adhesives used in catheter coatings may themselves significantly dilute the concentration of the therapeutic agent. Finally, thermal and luminous energy required to melt and bond coatings such as macro-aggregated albumin, to reduce tissue mass by ablation, and to inhibit restenosis by cytotoxic irradiation may also cause damage to blood vessels.

U.S. Pat. No. 5,470,307 to Lindall discloses a low-profile catheter system with an exposed coating containing a therapeutic drug agent, which can be selectively released at a remote tissue site by activation of a photosensitive chemical linker. In the invention disclosed by Lindall, the linker is attached to the substrate via a complementary chemical group, which is functionalized to accept a complementary bond to the therapeutic drug agent. The drug agent is in turn bonded to a molecular lattice to accommodate a high molecular concentration per unit area and the inclusion of ancillary compounds such as markers or secondary emitters. Although U.S. Pat. No. 5,470,307 to Lindall describes significant improvements over previous catheter-based drug delivery systems, the disclosed invention nonetheless has numerous problems. First, in common with other currently used endovascular access devices, such as catheters, microcatheters, and guidewires, the catheter tip is difficult to see on MRI because of inadequate contrast with respect to surrounding tissues and structures. This makes accurate localization difficult and degrades the quality of the diagnostic information obtained from the image. Thus, one objective of the present invention is to provide for an MR-compatible and visible vascular access device that significantly improves the efficacy and safety of cerebroendovascular drug delivery using MR guidance and/or non-linear magnetic stereotaxis, e.g., for retroperfusion therapies.

Any material that might be added to the structure of a pliable catheter in order to make it MR visible must not make the catheter magnetically susceptible, or imaging artifacts could be introduced during the MR process. Moreover, forces might be applied to such a catheter by the magnetic manipulation coils of the nonlinear magnetic stereotaxis system. In either case, the safety and efficacy of the procedure might be jeopardized, with resulting increased risk to the patient. Also, an MR-visible catheter must be made of material that is temporally stable, of low thrombolytic potential, and which is unlikely to damage any scar tissue formations if it is to be left indwelling in either the parenchymal tissues or the cerebral vasculature.

Guidewires are usually made of radio-opaque material so that their precise location can be identified during a surgical procedure through fluoroscopic viewing. Exemplary of guidewires used under X-ray viewing is the guidewire disclosed by LeVeen, U.S. Pat. No. 4,448,195, in which a radio-opaque wire can be identified on fluoroscopic images by metered bands placed at predetermined locations. The U.S. Pat. No. 4,922,924, awarded to Gambale et al. discloses a bifilar arrangement whereby radio-opaque and radiotransparent filaments are wrapped on a mandril to form a bifilar coil which provides radio-opaque and radiotransparent areas on the guide wire. U.S. Pat. No. 5,569,197 to Helmus and Forman discloses a drug delivery guidewire formed of super elastic materials which can be used as a drug delivery device in thrombolytic and other endovascular procedures. However, all of these guidewire materials are difficult to see on MR images because they fail to produce sufficient contrast with respect to the surrounding body tissues. This lack of MR visibility is also a problem for most commercially available catheters, microcatheters and shunts.

Attempts to visualize endovascular devices in MR imaging have generally been based on the passive susceptibility artifacts produced by the device when exposed to the MR field. Image distortion may include general signal loss, regional signal loss, general signal enhancement, regional signal enhancement, and increased background noise. U.S. Pat. No. 4,572,198 to Codrington provided for conductive elements, such as electrode wires, for systematically changing the magnetic field in a defined portion of the catheter to yield increased MR visibility of that region of the catheter. However, the presence of conductive elements in the catheter also introduces increased electronic noise and the possibility of Ohmic heating, and these factors have the overall effect of degrading the quality of the MR image and raising concerns about patient safety.

U.S. Pat. Nos. 5,154,179 and 4,989,608 to Ratner disclose the incorporation of paramagnetic material into endovascular devices in order to make the devices visible under MR imaging. However, these patents do not provide for artifact-free MR visibility in the presence of rapidly alternating magnetic fields, such as would be produced during echo-planar MR imaging pulse sequences used in real-time MR guidance of endovascular procedures. Nor do these patents teach a method for monitoring with MR visible catheters the outcomes of cerebroendovascular therapeutic interventions; for example, embolotherapy of cerebral aneurysms or arteriovenous malformations. Ultrafast imaging sequences generally have significantly lower spatial resolution than conventional spin-echo sequences. The magnetic susceptibility artifact produced by the device must be small enough not to obscure surrounding anatomy, or mask low-threshold physiological events that have an MR signature, and thereby compromise the physician's ability to perform the intervention.

A second problem with currently available endovascular devices relates to whether they can be used safely with high speed MR imaging procedures. The force on a ferromagnetic or permanent magnetic object in a magnetic field is, to a good approximation, given by the product of the object's magnetic dipole moment and the gradient of the magnetic field. Thus, it is important that endovascular devices used under MR guidance are MR-compatible in both static and time-varying magnetic fields. Similar considerations call for such devices to be compatible with the fields produced by the magnetic stereotaxis system, too. Although the mechanical effects of the magnetic field on ferromagnetic devices present the greatest danger to patients through possible unintended movement of the devices, tissue and device heating may also result from radio-frequency power deposition in electrically conductive material located within the imaging volume. Consequently, all cables, wires, and devices positioned within the MR imager or the magnetic stereotaxis system must be made of materials that have properties that make them compatible with their use in human tissues during MR imaging procedures or magnetic stereotaxis procedures.

U.S. Pat. No. 5,647,361 to Damadian discloses a catheter with guidewire whose position can be precisely controlled by piezoelectric actuators. However, unlike the present invention, the invention disclosed by Damadian does not provide for in vivo magnetic manipulation and selective navigation of blood vessels and bulk-tissue movement in the brain.

In the method of the invention, a retroperfusion catheter or other drug delivery device is placed by nonlinear magnetic stereotaxis, and is subsequently visualized and localized by its susceptibility artifacts on both conventional spin-echo and ultra-fast imaging sequences. Alternatively, in another method of the invention, the drug delivery device is visualized by the presence of one or more MR visible microcoils placed along the distal axis of the microcatheter. Imaging for visualization purposes is done after positioning of the microcatheter by nonlinear magnetic stereotaxis. MR visibility is variably adjustable based on requirements related to degree of signal loss for device localization and positioning, enhancement along the shaft of the device, enhancement around the body of the device, visibility of the proximal and distal ends of the device, degree of increased background noise associated with the device movement, and other factors which either increase or suppress background noise associated with the device.

The method of the invention can be used within a wide range of medical procedures as in, for example, a) providing for a temporary life-support system in stroke patients based on microcatheter retroperfusion of acutely ischemic brain tissue using nonlinear magnetic stereotaxis and MR imaging and/or X-ray guidance; b) for catheter-based administration of thrombolytic agents, MR-visible contrast media, or cerebroprotective anti-ischemia drugs, such as sodium and calcium neuronal membrane channel blockers, NMDA antagonists, glycine partial agonists, adenosine agonists and antagonists, calpain inhibitors, endothelin antagonists, anti-adhesion antibodies, antiphospholipid antagonists, and nitric oxide derivatives linked to blood-brain barrier transport vectors, such as liposomes, or perhaps to blood-brain barrier permeabilizing agents; c) for pre- and post-surgical endovascular treatment of tumors of the brain by acute, subacute and chronic infusion of therapeutic drug agents, neurotoxins, anti-angiogenesis factors, devascularization embolotherapy agents, anti-emetics, and anti-nausea agents linked to blood-brain barrier transport vectors, such as liposomes or blood-brain barrier permeabilizers; d) the catheter device can be used as a modified stent device to preserve the patency of intracranial venous blood vessels and sinuses which are either blocked by plaques or mechanically compressed by brain tumors, trauma, infection, or edematous masses; e) the MR-visible drug delivery device can also be used to treat non-ischemic cerebral lesions, such as the plaques associated with multiple sclerosis and Alzheimer's disease, by targeted endovascular or intraparenchymal injection or infusion of neuropeptides, monoclonal antibodies and other gene-targeted therapies, growth factors, and other therapeutic agents, which may be linked to various blood-brain transport vectors, such as liposomes or blood-brain barrier permeabilizers.

In one practice of the method of the invention, a multiple-lumen MR-visible microcatheter is directed into the venous neurovasculature or cerebral sinuses under nonlinear magnetic stereotaxis and its location is verified by MR or X-ray imaging.

The walls of the outer catheter are made of MR-compatible materials such as, but not limited to elastomeric hydrogel, polymers (thermoset or thermoplastic), composites, fabric, reinforced film, or similar material, which have an intrinsic elastic memory which can be activated by increased temperature, surface wetting, or decreased pH. The outer catheter has an adjustable stiffness which provides uniform circumferential contact with the vessel endoluminal surface, and thereby enables dynamic compliance matching with the intracranial or extracranial vessel undergoing therapy. In one preferred embodiment, the exit port on the microcatheter tip can also expanded up to two gauge sizes when hydrated or otherwise activated to improve the efficacy of endovascular retroperfusion of injured neuronal tissues.

In the general practice of the method of the invention, the MR-visible device, for example, a retroperfusion microcatheter, can be positioned in the venous intracranial circulation or dural sinuses under nonlinear magnetic stereotaxis and/or MR-imaging guidance. Cerebral delivery of drug agents or other biological materials is then monitored using contrast-enhanced magnetic susceptibility MR imaging or by active visualization via RF-Microcoils placed near the distal tip of the catheter. In cases of microcatheter migration, misplacement, disengagement, or compliance mismatch, the microcatheter can be retrieved and then subsequently repositioned by magnetic manipulation with minimal tissue damages. The MR-visible drug solutions may contain sterically stabilized liposomes, with lipophilic or hydrophilic chelators, such as DTPA on phosphatidyl ethanolamine or steric acid embedded within the external bilayer, or double-label liposomes that chelate a T2-sensitive metal ion within the internal aqueous space and another T1-sensitive metal ion on the outside surface, or liposomes which contain 100–1000 nm diameter bubbles of, for instance, argon, carbon dioxide, or air, as a contrast agent. Real-time contrast-enhanced magnetic-susceptibility-based MR imaging may be used to visually monitor the progress of neurovascular therapy. Changes in cerebral tissue perfusion are evaluated by bolus intravenous and intra-arterial injections of magnetic susceptibility contrast media, such as DyDTPA-BMA and GdDTPA-BMA, in combination with dynamic echo-planar MR imaging methods. Changes in cerebral perfusion are also evaluated by timed infusion of MR-visible sterically stabilized liposomes, with lipophilic or hydrophilic chelators, including the conjugation of DTPA on phosphatidyl ethanolamine or steric acid, embedded within the external bilayer. Cerebral perfusion is also evaluated with MR imaging following intravascular infusion of double-label liposomes that chelate a T2-sensitive metal ion within the internal aqueous space, and a T1-sensitive metal ion on the outside membrane surface. In another general embodiment the neurovascular device provides a temporary life support system in acute stroke patients by providing a device for retroperfusion of acutely ischemic brain under MR Imaging guidance, which can also monitor venous pressures and provide for pulsed-air inflation of an MR-visible angioplasty balloon at the distal end of the catheter.

With reference to FIG. 1 of the drawings, in the method of the invention the MR-visible microcatheter 1 has a shaft 2 made by conventional single extrusion technology of fluorinated ethylene-propylene copolymer, polytetrafluoroethylene, polychlorotrifluoroethylene, or similar commercially available material. From this example, the catheter would taper at the distal end 3 to about 0.020 and hence will accept a 0.018 guide- or pusher-wire 4 for mechanical advancement into the cerebrovasculature during nonlinear magnetic stereotaxis procedures. There may be approximately 0.5 to 20 cm (preferably from 0.5 to 3 cm) distal segment 7 made of hydrophilic cross linked polyurethane polymer containing polyoxyethylene and polyoxyethylene blocks, or from an elastomeric hydrogel formed from a polyurethane diacrylate composition, or from a multiple phase polymeric composition having a non-hydrophilic phase and hydrophilic phase in various preparations. In the method of the invention, the distal catheter segment 7 of the device has a softening index which can be programmed to change by 5- to 100-fold, and a physical expandability index which can be programmed to change by 1- to 3-fold over 3 min to 5 hours. In addition, the material used in the distal catheter segment 7 is non-thrombogenic and biocompatible, and has surface characteristics which bind and release drugs in a variably programmed manner. The catheter 1 which might be used for retroperfusion has a magnetic tip which allows it to be steered during nonlinear magnetic stereotaxis procedures. Both the catheter 1 and guide- or pusher-wire 4 have a linearly arranged array of radio-opaque and MR-visible markers 6 disposed at the distal end to provide easily identifiable reference points for trackability and localization under MR imaging and X-ray fluoroscopy. The microcatheter 1 can also be made from any of the well-known soft, biocompatible plastics used in catheter fabrication such as Percuflex, a trademarked plastic manufactured by Boston Scientific Corporation (Watertown, Mass.). When the catheter 1 is inserted into a patient, the distal markers 6 will be identifiable in an MR image and by X-rays, as will each of the other markers in the assembly. They can be formed of the well known radio-opaque materials such as gold, platinum or tantalum. An osmotic pump 7 and source of drug 8 is also shown.

With reference to FIG. 2 of the drawings, the microcatheter device 1 is also employed to deliver pharmacologic therapies, in order to reduce morbidity and mortality associated with cerebral ischemia, intracranial vasospasm, subarachnoid hemorrhage, and brain tumors. In the method of the invention, an MR-compatible osmotic pump (not shown) is connected via flexible MR-compatible tubing 2 to a device 1 such as a variable-length, concentric, MR-visible microdialysis probe with a variable molecular weight cut-off membrane or other infusion device which is directed by nonlinear magnetic stereotaxis, MR guidance, or by more conventional methods, to the site of the lesion within the central nervous system. The device 1 comprises a magnetic tip 5 restrained by a hole 8 at the distal end of the device 1. A segment 9 allows the release of drug 10 (shown as dotted area) into a patient. Marker areas 6 are shown, as is a microcatheter with its own marker areas 6 which can be inserted into the device 1.

With reference to FIG. 2 of the drawings, in the method of the invention, surface modifications of the material components of the device 1 which will be considered a dialysis probe in this description, enables timed-release kinetics of MR-visible biologic response modifiers, including peptide macromolecules. The osmotic pump (not shown) circulates a therapeutic drug solution 11 containing an MR-visible contrast agent 12 through the walls of the dialysis fiber or other infusion device into the brain at rates between 0.01 nanoliters per hour to 10 microliters per minute. In the method of the invention, the MR-visible solution contains sterically stabilized liposomes, with lipophilic or hydrophilic chelators, such as DTPA on phosphatidyl ethanolamine or steric acid embedded within the external bilayer, or double-label liposomes that chelate a T2-sensitive metal ion within the internal aqueous space and another T1-sensitive metal ion on the outside membrane surface, or liposomes which contain 100–1000 nm diameter bubbles, for example of argon, carbon dioxide, or air, as a contrast agent.

With reference to FIG. 3 of the drawings, in the method of the invention, the delivery and distribution kinetics of intracerebrovascular, intrathecal, and intraparenchymal injections or infusions of drug agents, and/or other diagnostic or therapeutic media can be monitored quantitatively and non-invasively using real-time contrast-enhanced magnetic susceptibility and diffusion-weighted MR imaging.

Another preferred aspect of construction of the delivery device 1 comprises the technology of Truwit and Liu described above where said device comprises a sheath or housing 2 comprising an element having at least one pair of opposed RF receiver microcoils 16 having a space 15 between each microcoil 16 of said pair of microcoils. The coils of said microcoils 16 may have diameters of less than 2.4 mm. The device may also comprise an element having at least one pair of opposed RF receiver microcoils having a space between each microcoil of said pair of microcoils, said RF receiver microcoils each comprising at least three individual coils, said at least three individual coils of said microcoils having spacing between adjacent microcoils so that spacing between at least two pairs of individual coils within said microcoils differ by at least 10%. Circuitry may be insulated within the device by providing the wires and circuits within different layers in a coaxial layering of components within the catheter. The device may also comprise a device with an element having at least one pair of opposed RF receiver microcoils having a space between each microcoil of said pair of microcoils, the RF receiver microcoils each comprising at least three individual windings, the at least three individual windings of said microcoils having spacing between adjacent windings so that spacing between at least two pairs of individual windings within the microcoils differ by at least 10%. A magnetic tip 5 is shown for use with nonlinear magnetic stereotaxis.

The entire coil can be a composite. In another words, the entire imaging coil can be made of multiple coil elements connected in series or in a phased array fashion for simultaneous imaging at multiple locations along a catheter. All of these multiple coils can be similar or different in their geometrical shape. The imaging coil can also be non-local. That is, the coil can be spatially distributed along a significant length of a catheter (especially by consideration of modeling as shown above). For this purpose, there are many choices for the active coil components: twisted wire, two parallel wire, coaxial cable, combinations of these, etc.

In addition to the variety available in the selection of the imaging coil component, various other components, such as micro-electrodes can be incorporated in the device for cell or membrane potential measurement, pressure/flow monitoring or other physiological monitoring and/or electrophysiological and/or stimulating purposes.

For optimal signal to noise ratio (S/N) or minimal resulting noise figure, the MR signal detected would preferably have an immediate amplification (e.g., preamplification) in a location as close as possible to the coil element. The practical catheter geometry does not provide enough room for using any conventional amplification components. For the purpose of minimizing the size of the electronic components which will be used for various signal preconditioning processes such as pre-amplification, we have introduced an integrated circuit module in close proximity to the imaging module. The integrated circuit module includes a pre-amplification device (or unit at RF frequency) and other auxiliary devices silicon or other semiconductor fabricated on a chip, which is preferably less than 4 $mm^2$ in size. The same integrated circuit module is preferred to be packaged in a small non-magnetic casing compatible in shape with a given instrument design. One of the most simple units may contain only a single FET element. With the help of the integrated circuit technology, more elements can be incorporated into one single silicon or other semiconductor module for building more complex circuitry to achieve a better performance.

The preferred transmission module is a portion of the flexible cable along the catheter for transmitting the RF signal detected for MR imaging from the coil to a remote terminal for further signal amplification and other required processing. In preferred design contemplations, all of the components of the cable are integrated into the catheter. One of the desired requirements for the cable is that it will introduce a minimal noise contamination as well as a low signal attenuation to the minute MR signal. The other desired requirement for the cable is that it will introduce a minimal hindrance to the flexibility and the stiffness of a catheter. For achieving these requirements, there are a number of the possible alternatives for the device as follows:

1) A tri-coaxial cable (a cable with a center line conductor surrounded by two concentric layers of shielding material). One variation of the cable is that the center conductor is wound in a helical fashion along the center axis of the cable.

2) A shielded twisted wire cable (a cable with two twisted wires at the center surrounded by a concentric layer of shielding material). One variation of the cable is that the two wires are wound in a spiral or helical fashion along the center axis of the cable.

3) A shielded parallel bi-polar cable (a cable with two parallel bi-polar wires placed symmetrically with respect to the center axis surrounded by a concentric layer of shielding material). One variation of the cable is that the two wires parallelly are wound in a spiral or helical fashion along the center axis of the cable.

The shielding layer can be a layer of braided thin conductive wires as well as a layer of metallic film, or any other shielding material (which may be grounded if desired) as understood in the art which may be provided in a dimension compatible with the practice of the present invention.

Yet another useful design is a concept of putting all the elements at the remote unit (or distal end). The schematic circuit diagram shown above in FIG. 3 includes an imaging coil (micro or macro), transmission line, phase shift network, tuning and decoupling circuit and balance (i.e., balanced/unbalanced impedance matching transformer). The Z denotes a tuning element (L or C) as a part of the decoupling circuit. The combined transmission line and phase shift network exhibits a quarter or half wavelength property.

The remote matching unit represents a device placed at the remote end of the device. This remote unit can be used as an extra tuning device for the imaging coil at the tip as well as a detuning (or decoupling) device. The remote match unit takes the effective impedance transformation of the transmission unit into consideration for the coil impedance matching and frequency tuning. In this design, both the transmission wire and the remote unit are used for accomplishing the tuning and detuning. In order to take advantage of the property of the transmission wire, the wire with a quarter wave or half wave length of the radio frequency of interest is used. Otherwise a transmission wire with a phase shift network which shows the same effective quarter wave or half wave length behavior can be used. The coil tuning can be accomplished with a capacitor or inductor. In addition, the size of the unit is not constrained geometrically. Since the device size for this module is not an issue, more conventional electronic components can be used. Depending on a specific design, the remote unit can be very important or of no importance.

Finally, the catheter tip has a stabilization mechanism incorporated. The preferred stabilization unit can be mechanically driven, or made of memory metal and controlled with an externally applied voltage signal.

As previously noted, it may be desirable to remove the magnetic tip used in the nonlinear magnetic stereotaxis positioning and guidance of the delivery device during the MR imaging and visualization step. It may also be desirable to be able to move that magnetic tip back into a movement effective position after the MR imaging to assist in further guidance or movement of the delivery device. This can be effected by any form of attachment or engagement of the tip to the catheter wherein the tip can be released or repositioned and then returned to an attached arrangement to the tip which attachment is of sufficient security as to enable movement, torque and application of directing or motivating forces to the catheter or delivery device. For example, in the simplest mode, the tip may be secured to the distal end of the device by tension on an elongated element holding the tip against an opening with a smaller diameter of the opening than the cross-section of the tip. The tip may be moved from the distal end by pulling on the elongated element, and then returned to the distal end after MR visualization by applying pushing tension on the elongated element again. Microminiature circuitry may also be used with the distal end to move the tip in a similar manner. A balloon system may be used whereby inflation of a balloon (with the tip on a surface of the balloon) will cause the expansion of the balloon to move the tip the expanded diameter of the balloon. A threaded engagement of the tip on the distal end of the delivery device (or at another guidance effective position) may be used, with unthreading, by the application of torque to the tip that may be used to temporarily free the tip, and reverse torque used to rethread the tip. This may be particularly effective where the tip lies completely within a threaded lumen, and rotation of the tip causes the tip to move in the desired direction within the lumen, first out of the image zone and then back into a desired position relative to effective guidance of the delivery device. This is most effective where movement out of the image zone would be in a direction away from the distal end of the tip. The tip may be slidably positioned on an outside surface or inside surface of the delivery device, and moved by appropriately applied forces back and forth over the surface of the delivery device. Where there is a porous or open area in the drug delivery device for allowing perfusion of drug along the sides of the device, the slidable tip may have a combined effect of non-linear magnetic stereotaxis guidance tip and protective cover/timed drug release activator for the delivery device.

As noted, microcircuitry may be used near or distant from the movable tip as a drive engine for any mechanical engagement to physically move the tip and reposition the tip, if desired. Material used to move the tip, secure the tip or the like, is preferably not strongly responsive to magnetic fields, and would preferably comprise polymeric or composite materials.

FIG. 4a shows a device 1 with a housing 2, a magnetic tip 20 nestling in the distal end 21 of the device 1 against an inside surface 24 of the housing 2. Marker areas 4 and 10 are shown separated over the lumen 14 of the device 1. FIG. 4b shows a different device 1 with an opening 26 at the distal end of the device 1.

We claim:

1. A catheter for use within cerebral blood vessels of an organism, the catheter comprising at least one lumen, and within the at least one lumen at least two microcatheters, with at least one of the at least two microcatheters being connected to a source of liquid material to be delivered to the organism and another of the at least two microcatheters being connected to a system capable of effecting a medical treatment other than delivery of the liquid.

2. The catheter of claim 1 wherein the medical treatment other then delivery of the liquid comprises stimulation of natural activities.

3. The catheter of claim 2 wherein at least one opposed pair of microcoils is present on the catheter.

4. The catheter of claim 1 wherein the medical treatment other then delivery of the liquid comprises stimulation of natural activities of chemical producing systems.

5. The catheter of claim 4 wherein at least one opposed pair of microcoils is present on the catheter.

6. The catheter of claim 4 wherein electronic circuitry is located within the catheter.

7. The catheter of claim 4 wherein at least one opposed pair of microcoils is present on the catheter.

8. The catheter of claim 1 wherein the medical treatment other then delivery of the liquid comprises removal of deposits of materials.

9. The catheter of claim 8 wherein the at least two microcatheters pass within the lumen, and exit holes are provided in the catheter for the at least two microcatheters.

10. The catheter of claim 9 wherein deflectors are present within the lumen for directing the at least two microcatheters through the holes.

11. The catheter of claim 1 wherein at least one opposed pair of microcoils is present on the catheter.

12. The catheter of claim 11 wherein electronic circuitry is located within the catheter.

13. The catheter of claim 1 wherein electronic circuitry is located within the catheter.

14. The catheter of claim 1 wherein the at least two microcatheters pass within the lumen, and exit holes are provided in the catheter for the at least two microcatheters.

15. The catheter of claim 14 wherein deflectors are present within the lumen for directing the at least two microcatheters through the holes.

16. The catheter of claim 1 wherein the medical treatment other than liquid delivery comprises an endovascularly therapeutic application.

17. The catheter of claim 1 wherein the medical treatment other than liquid delivery comprises a pressure or flow measurement system.

18. The catheter of claim 1 wherein the medical treatment other than liquid delivery comprises a physiology monitoring system.

19. The catheter of claim 1 wherein the medical treatment other than liquid delivery comprises electrical stimulation.

20. The catheter of claim 1 wherein the medical treatment other than liquid delivery comprises dispersing of deposits.

21. The catheter of claim 1 also containing at least one optical fiber.

22. The catheter of claim 1 wherein the medical treatment other than liquid delivery comprises a balloon catheter.

23. The catheter of claim 1 wherein the medical treatment other than liquid delivery comprises an ablation system.

24. The catheter of claim 1 wherein the medical treatment other than liquid delivery comprises a cytotoxic irradiation system.

25. The catheter of claim 1 wherein the medical treatment other than liquid delivery comprises an electrophysiological monitoring system.

26. The catheter of claim 1 wherein electronic circuitry is located external to the catheter.

27. The catheter of claim 1 wherein the medical treatment other than liquid delivery comprises a diagnostic treatment.

28. The catheter of claim 1 wherein the medical treatment other than liquid delivery comprises microwave heating and the catheter comprises a microwave coil.

29. The catheter of claim 1 wherein the medical treatment other than liquid delivery comprises a liquid removal system.

30. The catheter of claim 1 wherein the medical treatment other than liquid delivery comprises a heating system.

31. A catheter for use within cerebral blood vessels of an organism, the catheter comprising at least one lumen, and within the at least one lumen at least two microcatheters, and a deflector within the lumen for deflecting microcatheters towards exit ports within the catheter.

32. A catheter for use within cerebral blood vessels of an organism, the catheter comprising at least one lumen, and within the at least one lumen at least two microcatheters, with at least one of the at least two microcatheters being connected to a source of liquid material to be delivered to the organism and another of the at least two microcatheters being connected to a system capable of effecting a medical treatment other than delivery of the liquid comprising stimulation of natural activities, wherein at least one opposed pair of microcoils is present on the catheter, and electronic circuitry is located within the catheter.

* * * * *